United States Patent [19]

Duck et al.

[11] Patent Number: 5,660,988
[45] Date of Patent: Aug. 26, 1997

[54] CYCLING PROBE CLEAVAGE DETECTION OF NUCLEIC ACID SEQUENCES

[75] Inventors: Peter Duck, Burnaby; John McNevin, Vancouver, both of Canada

[73] Assignee: ID Biomedical Corporation, Burnaby, Canada

[21] Appl. No.: 483,743

[22] Filed: Jun. 7, 1995

Related U.S. Application Data

[63] Continuation-in-part of Ser. No. 153,349, Nov. 17, 1993, abandoned.

[51] Int. Cl.[6] .................................................. C12Q 1/68
[52] U.S. Cl. .................................................. 435/6; 536/24.3
[58] Field of Search ................................ 435/6; 536/24.3

[56] References Cited

U.S. PATENT DOCUMENTS

| | | | |
|---|---|---|---|
| 4,358,535 | 11/1982 | Falkow et al. | 435/5 |
| 4,362,867 | 12/1982 | Paddock | 536/27 |
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,736,866 | 4/1988 | Leder et al. | 800/1 |
| 4,876,187 | 10/1989 | Duck et al. | 435/6 |
| 5,011,769 | 4/1991 | Duck et al. | 435/6 |
| 5,149,797 | 9/1992 | Pederson et al. | 536/27 |

FOREIGN PATENT DOCUMENTS

| | | | |
|---|---|---|---|
| 067 597 A1 | 12/1982 | European Pat. Off. | C07H 21/00 |
| 117 440 A1 | 9/1984 | European Pat. Off. | C07H 21/00 |
| 227 976 A2 | 7/1987 | European Pat. Off. | C07H 21/00 |
| 329 311 A1 | 8/1989 | European Pat. Off. | C12Q 1/68 |
| WO 84/03520 | 9/1984 | WIPO | C12Q 1/68 |
| WO 89/09284 | 10/1989 | WIPO | C12Q 1/68 |
| WO 89/10415 | 11/1989 | WIPO | C12Q 1/68 |
| WO 91/06679 | 5/1991 | WIPO | C12Q 1/68 |
| WO 91/17264 | 11/1991 | WIPO | C12Q 1/68 |
| WO 92/02638 | 2/1992 | WIPO | C12Q 1/68 |
| WO 93/20233 | 10/1993 | WIPO | C12Q 1/68 |
| WO 95/00667 | 1/1995 | WIPO | C12Q 1/68 |
| WO 95/05480 | 2/1995 | WIPO | C12Q 1/68 |

OTHER PUBLICATIONS

Goodchild, J., "Conjugates of oligonucleotides and modified oligonucleotides: A review of their synthesis and properties," *Bioconjugate Chemistry* I(3): 165–187, 1990.

Prosser, J., "Detecting single–base mutations," *Trends in Biotechnology* 11:238–246, 1993.

*Primary Examiner*—Kenneth R. Horlick
*Assistant Examiner*—Joyce Tung
*Attorney, Agent, or Firm*—Seed and Berry LLP

[57] ABSTRACT

A method for determining whether a selected nucleic acid molecule differs by one or more nucleotides from a desired sequence (the desired sequence may be defined to be either a native (e.g., wild type) or non-native (e.g., mutant) nucleotide sequence). The potential difference between the selected nucleic acid molecule and the desired nucleic acid sequence may be due to a germ or somatic mutation and may be, for example, a substitution, deletion addition or transversion of one or more nucleotides. Thus, for example, the method is useful for detection of mutations in oncogenes or mutations in other genes of interest, such as the transmembrane conductance regulator gene, which is implicated in cystic fibrosis.

18 Claims, 9 Drawing Sheets

Probe Linked
via tether to
RNASE H

Target

Probe Fragment
accumulation
and detection

——————  Target DNA sequence
Target

DNA-RNA-DNA Probe covalently
linked via tether to RNASE H (———▶)

Probe Fragment accumulation and detection

CYCLING PROBE CLEAVAGE DETECTION OF NUCLEIC ACID SEQUENCES

CROSS-REFERENCE TO RELATED APPLICATIONS

This application is a continuation-in-part of U.S. application Ser. No. 08/153,349, filed Nov. 17, 1993, abandoned.

TECHNICAL FIELD

The field of the present invention is the detection of desired nucleic acid sequences, particularly when such sequences comprise a portion of a lengthy nucleic acid sequence.

BACKGROUND OF THE INVENTION

Nucleic acid probes are typically single strands of DNA or RNA that are capable of specifically binding to a complementary nucleic acid. Thus, such probes are used in the biotechnology field to seek out and detect a desired nucleic acid.

Current nucleic acid probe methodology, which may detect a single base mutation under very stringent conditions, typically involves attaching a selected nucleic acid molecule to a nitrocellulose filter by bringing it into contact with the filter directly or via the Southern transfer technique from an agarose gel. The selected nucleic acid molecule is then denatured and the filter is baked to ensure firm attachment. Generally, the preparation of the nucleic acid molecule and the running of the gel is a time-consuming, costly process requiring a reasonably high technical skill level.

The next step is to prepare a probe nucleic acid molecule, by radioactively labeling a specific nucleic acid molecule using procedures well known in the art, such as nick translation or polynucleotide kination. The probe nucleic acid molecule hybridizes with the bound selected nucleic acid molecule at a suitable temperature, typically for several hours. The probe nucleic acid molecule hybridizes with any bound selected nucleic acid molecule that has complementary base sequences. Extraneous material, including unbound probe nucleic acid molecule, is then washed away from the filter and the filter is then exposed to film sensitive to the radioactive label.

In certain instances, the amount of selected nucleic acid probe may be too small for routine hybridization analysis. However, the quantity of a selected nucleic acid molecule that may have a mutation to one or more bases may be increased by subjecting the selected nucleic acid molecule to polymerase chain reaction ("PCR"), as disclosed in U.S. Pat. No. 4,683,195 (Mullis et al.). (Throughout this specification, reference is made to various patents and publications. The disclosures of all such patents and publications in their entireties are expressly incorporated herein by reference.) PCR comprises treating separate complementary strands of the selected nucleic acid molecule with a molar excess of 2 oligonucleotide primers. The primers permit formation of complementary primer extension products, which then act as templates for a next round of synthesizing the selected nucleic acid sequence, thus, the sequence is amplified and may then be detected. A disadvantage of this process is the requirement for thermal cycling, and the potential for carryover contamination due to amplification of the selected nucleic acid molecule, itself. The PCR-amplification products may then be screened with a probe, as described above. In an alternative approach, the PCR-amplification products could be sequenced using traditional methods well known in the art, such as dideoxynucleotide sequence analysis.

In an alternative approach, U.S. Pat. Nos. 4,876,187 and 5,011,769 (both to Duck et al.) disclose nucleotide sequences having scissile linkages that are useful for the detection of selected nucleic acid sequences. However, neither patent is specifically directed to the detection of a single nucleotide mismatch between a desired sequence and other sequences present in a sample.

SUMMARY OF THE INVENTION

The present invention provides a new, highly sensitive method for determining whether a selected nucleic acid molecule differs by one or more nucleotides from a desired sequence. The new method does not require thermal cycling or expensive apparatus, and may detect even a single desired nucleic acid molecule in a sample containing a multitude of nucleic acid molecules of other sequences.

In one aspect, the present invention provides methods of determining whether a selected nucleic acid molecule contains a suspected difference from a desired sequence comprising the following steps. (A) incubating the selected nucleic acid molecule with a nucleic acid probe containing a scissile linkage, the nucleic acid probe being complementary at the scissile linkage to the desired sequence and the length of the scissile linkage determined by the suspected difference, under conditions suitable for specific hybridization of the selected nucleic acid molecule with the nucleic acid probe to produce a hybrid. (B) contacting the hybrid with an excising agent capable of cleaving the nucleic acid probe at the scissile linkage when the nucleic acid probe is specifically hybridized at the scissile linkage to the selected nucleic acid molecule, wherein upon such cleavage of the nucleic acid probe at the scissile linkage, one or more fragments of the nucleic acid probe are released from the hybrid. And, (c) then detecting and quantitating or quantifying the release of fragments of the nucleic acid probe, and therefrom determining whether the selected nucleic acid molecule differs from the desired sequence. Preferably, the detecting step includes the quantification of the rate of release of the fragments.

In a particularly preferred embodiment, the methods comprise performing two (or more) sets of reactions in different reaction vessels, wherein one of the reactions is performed using a nucleic acid probe that is complementary to the desired sequence for the selected nucleic acid molecule, and the second (or more) reactions is performed using a nucleic acid probe that is complementary to the suspected difference. Preferably, the desired sequence is identical to a native (or wild type) sequence, typically for a known gene. The presence or absence of the suspected difference can be determined by comparing said detection and quantitation of each the reactions.

In a preferred embodiment, the scissile linkage comprises RNA and the excising agent comprises RNase H. In an alternative preferred embodiment, the scissile linkage comprises DNA and the fragments of the nucleic acid probe that are adjacent to the scissile linkage comprise one or more of (a) modified DNA that cannot be effectively excised by the excising agent; and (b) RNA.

The selected nucleic acid molecule may be derived from a diploid or polyploid organism. The selected nucleic acid molecule may also be derived from a haploid cell, such as a sperm cell, an ova, or a unicellular organism. The selected nucleic acid molecule may be present in a sample with other nucleic acid molecules from the organism, as well as other nucleic acid molecules from other organisms. Further, where the selected nucleic acid molecule contains the desired sequence, the desired sequence may be present in either a homozygous or heterozygous state in the diploid or polyploid organism.

In a preferred embodiment, steps (a)–(c) above are repeated. In such an embodiment, it is preferred that a single copy of the selected nucleic acid molecule hybridizes with, and is then released from, multiple copies of the nucleic acid probe. (Where the selected nucleic acid molecule does not contain the desired sequence, then there will either be no hybridization or no cleavage at the scissile linkage, and thus no release of probe fragments, so steps (a)–(c) will not be able to repeat.)

In a further aspect, the present invention provides a method of determining whether a selected nucleic acid molecule contains a suspected difference form a native nucleotide sequence, comprising the following steps: (a) incubating the selected nucleic acid molecule with a nucleic acid probe containing a scissile linkage, the nucleic acid probe being complementary at the scissile linkage to the native nucleotide sequence and the length of the scissile linkage determined by the suspected difference, under conditions suitable for specific hybridization of the selected nucleic acid molecule with said nucleic acid probe to produce a hybrid; (b) contacting the hybrid with an excising agent capable of cleaving the nucleic acid probe at the scissile linkage when the nucleic acid probe is specifically hybridized at the scissile linkage to the selected nucleic acid molecule, wherein upon cleavage of the nucleic acid probe at the scissile linkage, one or more fragments of the nucleic acid probe are released from the hybrid; and (c) detecting and quantitating the released fragments of the nucleic acid probe, and therefrom determining whether the selected nucleic acid molecule differs from the native nucleotide sequence.

In a preferred embodiment, the selected nucleic acid molecule includes a somatic mutation or germ cell or germ line, preferably germ line, mutation at a site where the scissile linkage of the nucleic acid probe is capable of hybridization. Further, it is preferred that the selected nucleic acid molecule be derived from an oncogene. In an alternative preferred embodiment, the selected nucleic acid molecule comprises at least a portion of the transmembrane conductance regulator gene, which gene is implicated in cystic fibrosis.

In a further aspect, the present invention provides a method of determining whether a selected nucleic acid molecule tends to induce cystic fibrosis by determining whether the selected nucleic acid molecule has a suspected difference from a native nucleotide sequence for the transmembrane conductance regulator gene at a site in the gene where mutation tends to cause cystic fibrosis, comprising the following steps: (a) incubating the selected nucleic acid molecule with a nucleic acid probe containing a scissile linkage, the length of the scissile linkage determined by the suspected difference, and the nucleic acid probe complementary at the scissile linkage to the native nucleotide sequence for the transmembrane conductance regulator gene, under conditions suitable for hybridization of the selected nucleic acid molecule with the nucleic acid probe to produce a hybrid; (b) contacting the hybrid under such conditions with an excising agent capable of cleaving the nucleic acid probe at the scissile linkage when the nucleic acid probe is specifically hybridized at the scissile linkage to the selected nucleic acid molecule, wherein upon cleavage of the nucleic acid probe at the scissile linkage, one or more fragments of the nucleic acid probe are released from the hybrid; and (c) detecting and quantitating the released fragments of the nucleic acid probe, and therefrom determining whether the selected nucleic acid molecule differs from the native nucleotide sequence for the transmembrane conductance regulator gene. Where a difference in the rate of production of fragments, or the final quantity of fragments, is observed, it is determined that the detected gene tends to induce cystic fibrosis.

In a preferred embodiment, the selected nucleic acid molecule is derived from a transmembrane conductance regulator gene that has been derived from a diploid animal, and the determining step further comprises determining whether the organism is (a) homozygous, with both alleles having a mutation in the transmembrane conductance regulator gene, (b) heterozygous, with one allele having a mutation in the transmembrane conductance regulator gene and the other allele containing a native nucleotide sequence for the transmembrane conductance regulator gene, or (c) homozygous, with both alleles having the native nucleotide sequence for the transmembrane conductance regulator gene.

These and other aspects of the present invention will become evident upon reference to the following description and attached drawings.

DETAILED DESCRIPTION OF THE INVENTION

Figure 1:
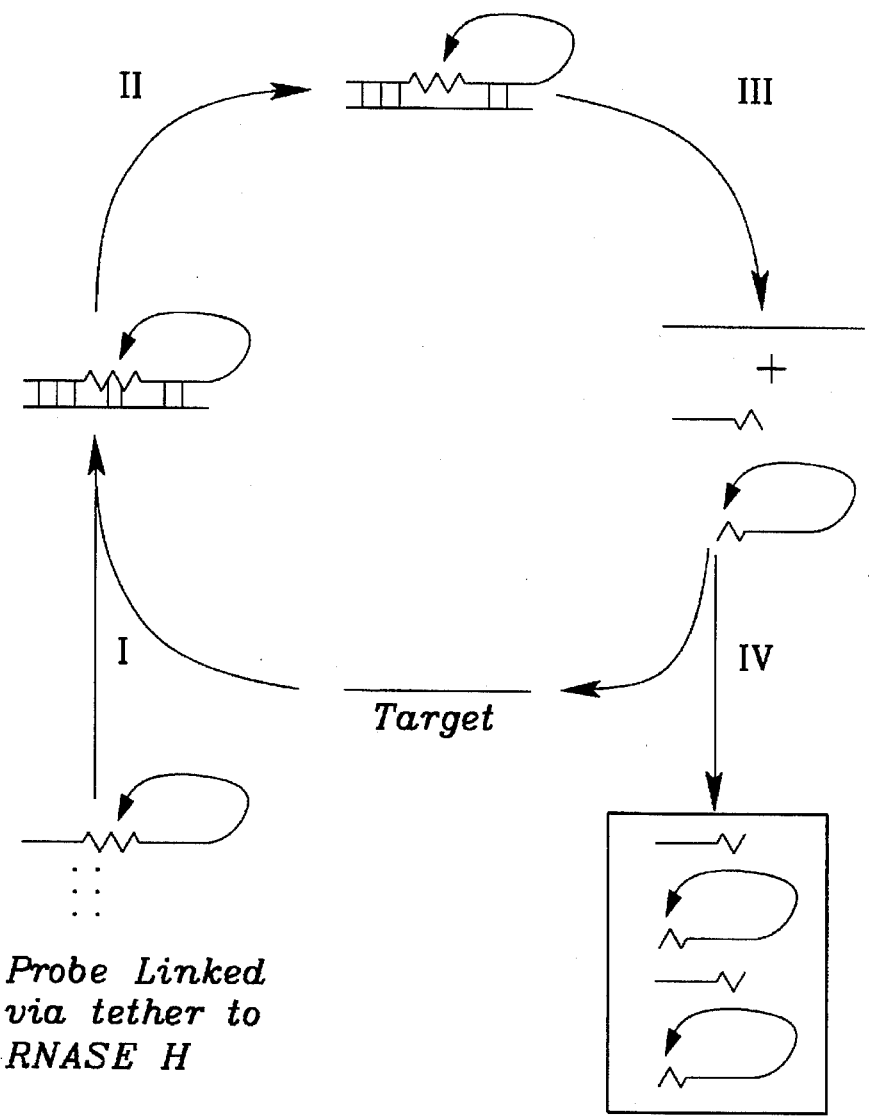
FIG. 1 is a schematic illustration of a cycling probe reaction utilizing a probe covalently linked to RNase H.
Figure 1:
Figure 2:
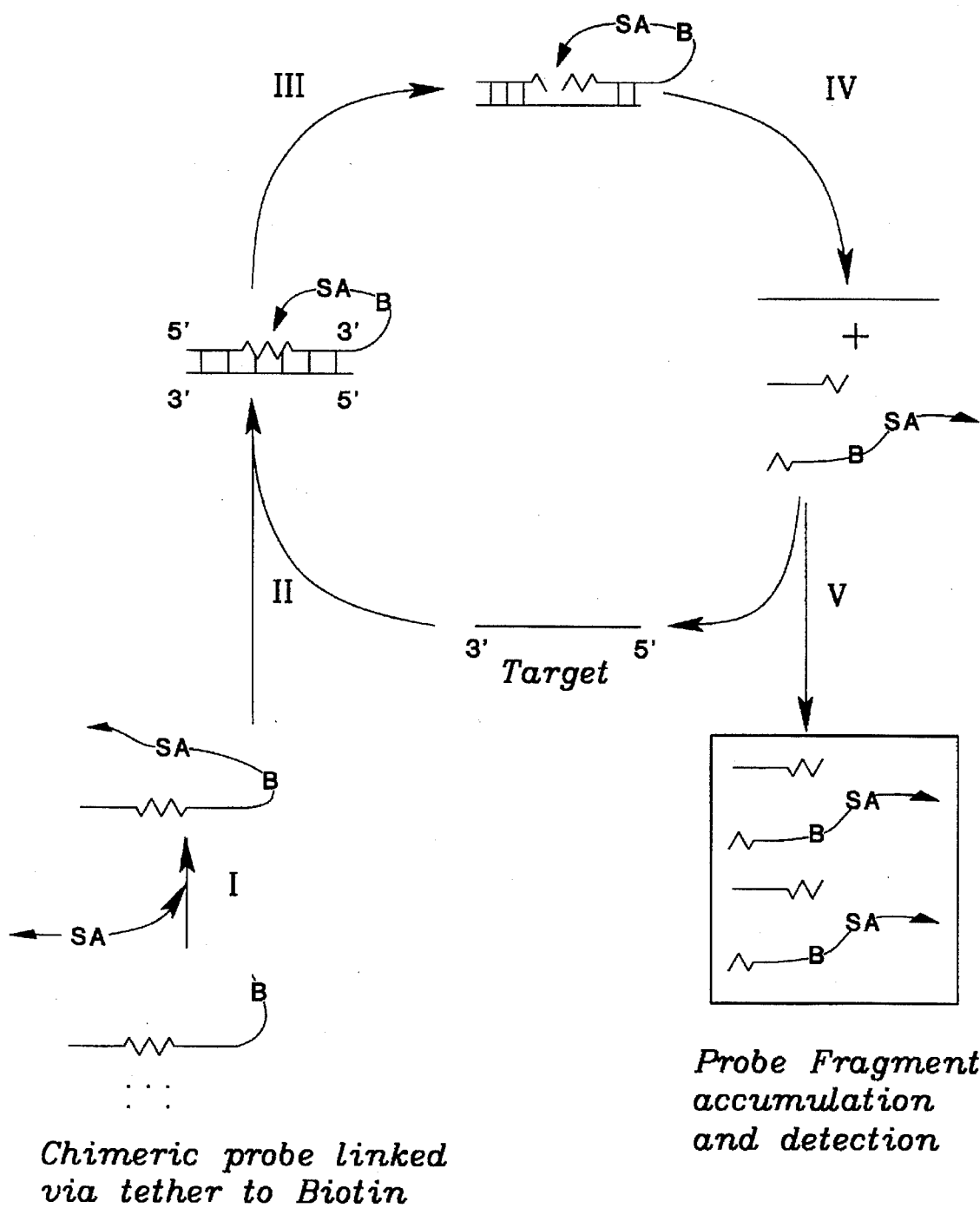
FIG. 2 is a schematic illustration of a cycling probe reaction utilizing a probe linked to RNase H through a biotin-streptavidin linkage.
Figure 3:
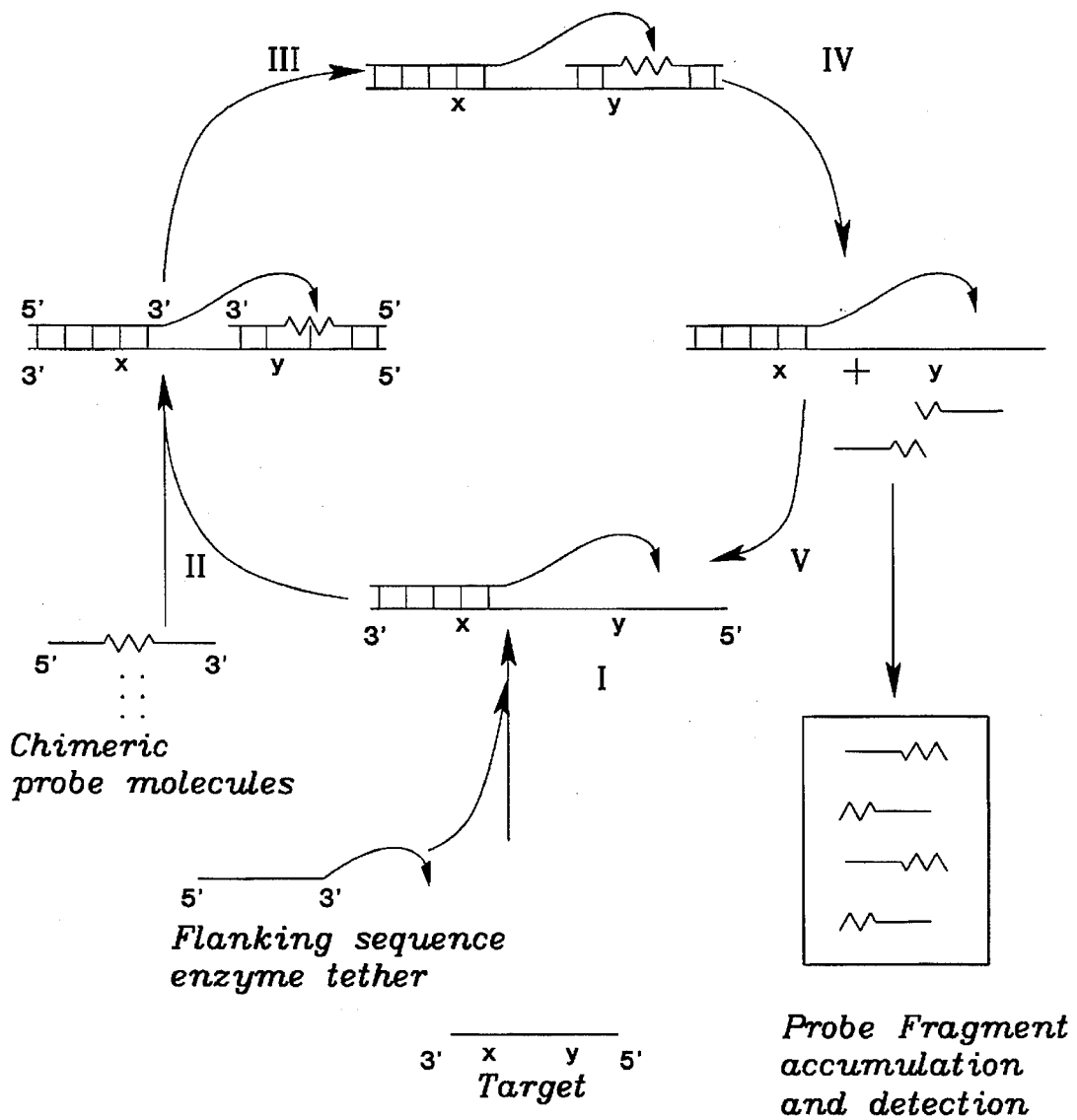
FIG. 3 is a schematic illustration of a cycling probe reaction utilizing adjacent sequence covalently linked to an enzyme.
Figure 4:
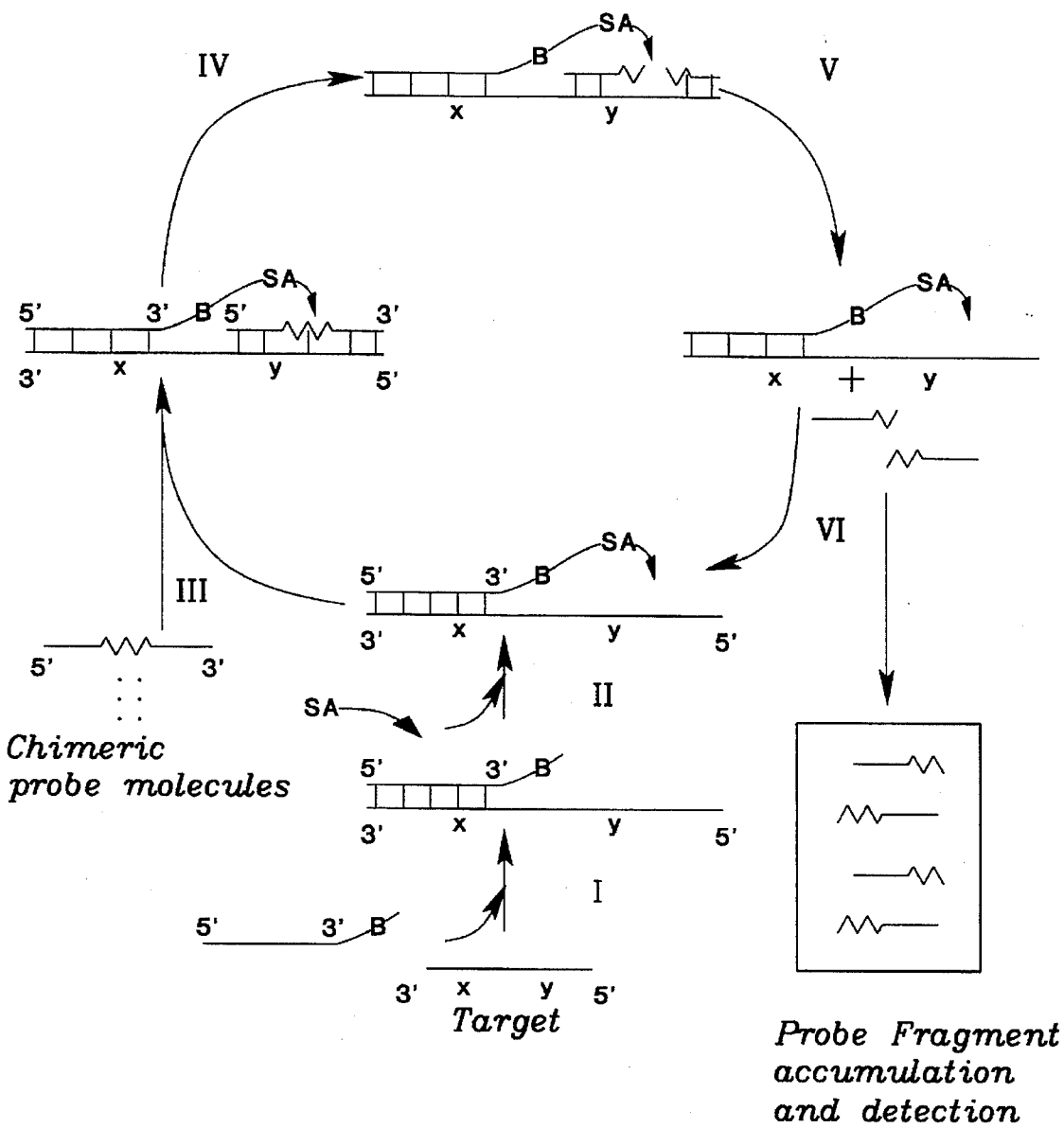
FIG. 4 is a schematic illustration of a cycling probe reaction utilizing an adjacent sequence linked to RNase H through a biotin-streptavidin linkage.
Figure 5:
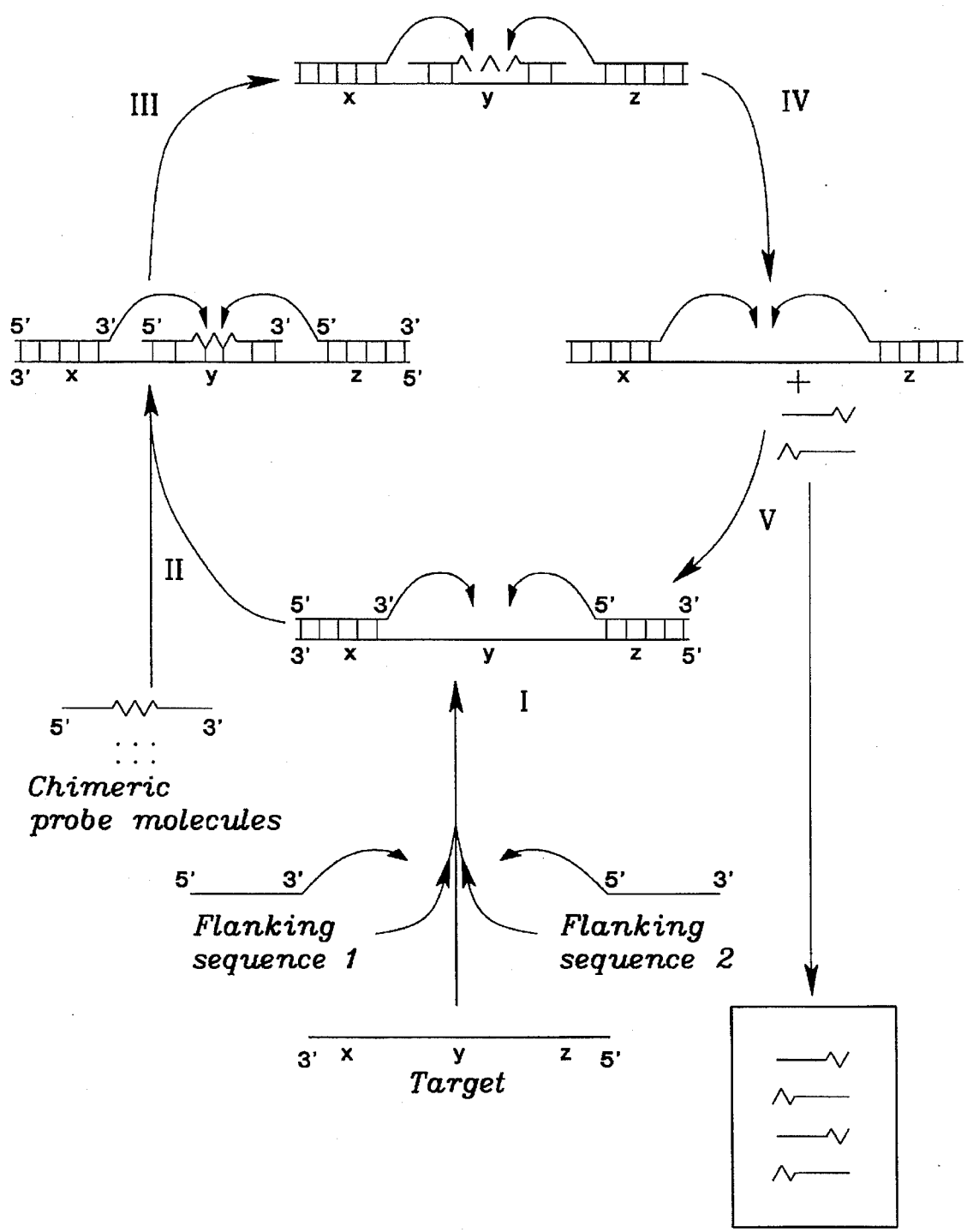
FIG. 5 is a schematic illustration of a cycling probe reaction utilizing two adjacent sequences, each of which have been linked to RNase H.
Figure 6:
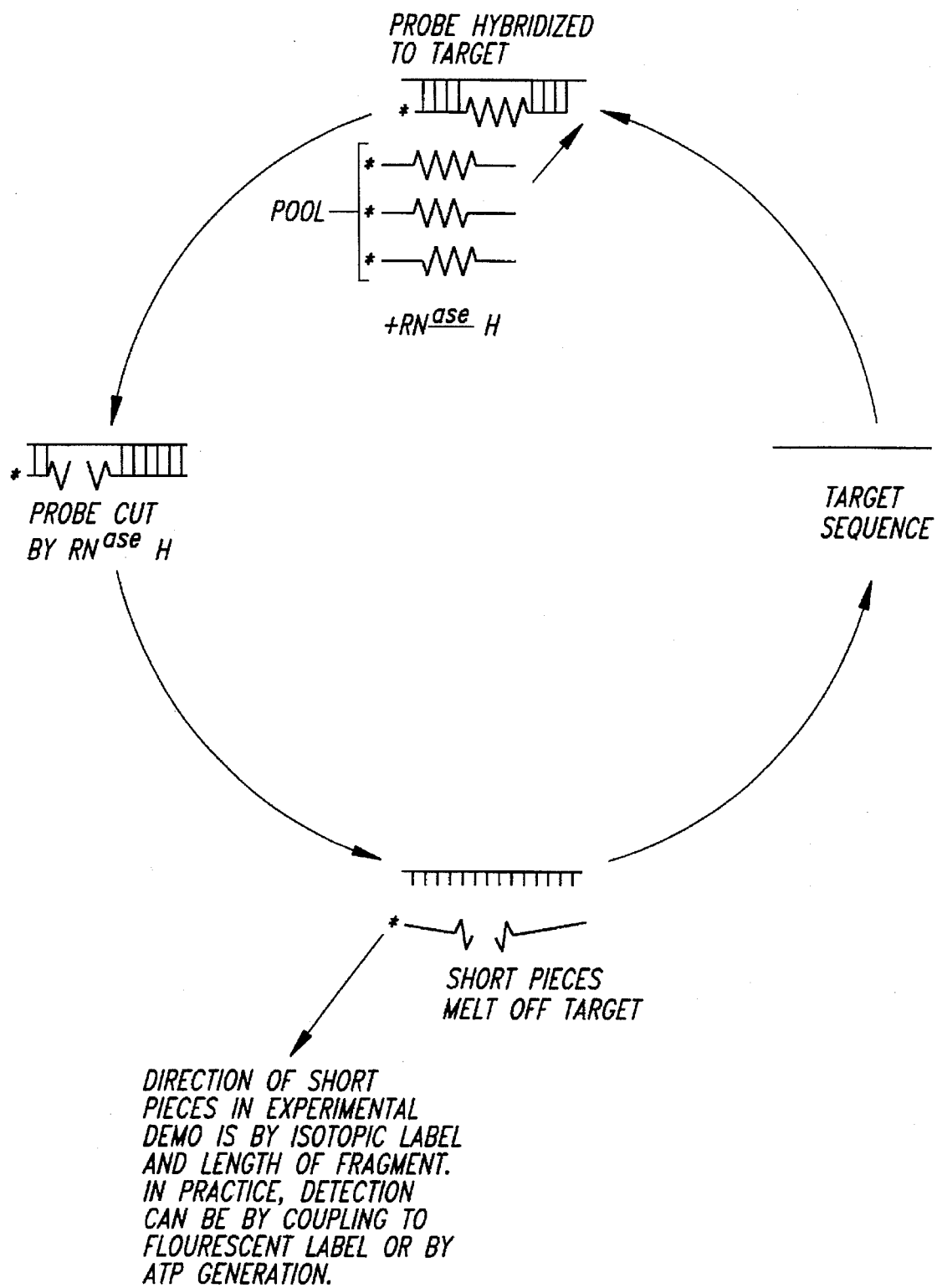
FIG. 6 is schematic illustration of a cycling probe reaction where the probe is not linked to an excising agent.

The present invention provides methods for determining whether a selected nucleic acid molecule differs by one or more nucleotides from a desired sequence (the desired sequence may be defined to be either a native (e.g., wild type) or non-native (e.g., mutant) nucleotide sequence). The suspected difference between the selected nucleic acid molecule and the desired nucleic acid sequence may be, for example due to a germ or somatic mutation and may be a substitution, deletion, addition or transversion of one or more nucleotides. Further, the suspected difference may include an entire mutation, or only a portion of a mutation. Thus, for example, the method is useful for the determination of mutations in oncogenes, such as mutations in the Ras, HER/neu2 or p53 genes. The method is also useful for the determination of mutations in other genes of interest, such as the transmembrane conductance regulator gene, which is implicated in cystic fibrosis, the hemoglobin genes, which are implicated in sickle cell anemia and thalessemia, and the various genes implicated in the hemophilias.

The methods of the present invention are particularly useful for determining whether a selected nucleic acid molecule has a 1, 2 or 3 nucleotide difference from the desired sequence, such as where the selected nucleic acid molecule has a single nucleotide substitution or a 3-nucleotide deletion. In a preferred embodiment, the selected nucleic acid molecule differs from the desired sequence and is located in and identified from a sample potentially containing a large population of nucleic acid molecules comprising the desired sequence.

The selected nucleic acid molecule may be chosen from a variety of nucleic acid molecules, including recombinant and machine-made nucleic acid molecules. Representative examples of selected nucleic acid molecules include nucleic acid molecules obtained from mammalian cells, fungal cells, bacterial cells, viruses, and plant cells. Preferred selected nucleic acid molecules are single-stranded, and may be unique to the target for which they allow detection. Methods for choosing and preparing preferred selected nucleic acid molecules, as well as methods for generating single-stranded selected nucleic acid molecules, may be readily accomplished by one of ordinary skill in the art given the disclosure provided herein (see generally, Sambrook et al., *Molecular Cloning: A Laboratory Manual* (2nd edition), Cold Spring Harbor Laboratory Press, 1989).

Accordingly, the present invention provides methods comprising the steps of: (a) incubating the selected nucleic acid molecule with a nucleic acid probe containing a scissile linkage, the nucleic acid probe being complementary at the scissile linkage to the desired sequence and the length of the scissile linkage determined by the suspected difference, under conditions suitable for specific hybridization of the selected nucleic acid molecule with the nucleic acid probe to produce a hybrid; (b) contacting the hybrid with an excising agent capable of cleaving the nucleic acid probe at the scissile linkage when the scissile linkage is specifically hybridized to the selected nucleic acid molecule, wherein upon cleavage of the nucleic acid probe at the scissile linkage one or more fragments of the nucleic acid probe are released from the hybrid; and (c) detecting and quantitating the released fragments of the nucleic acid probe, and therefrom determining whether the selected nucleic acid molecule differs from the desired sequence. FIGS. 1–6 schematically depict various embodiments of such methods. The perturbation of the rate of cleavage can also be caused by mismatches not actually within the scissile linkage, but that are near (typically within one or two bases) the scissile linkage).

In some embodiments, the rate of generation of released fragments is such that the methods provide, essentially, a yes/no result, whereby the detection of virtually any released fragment indicates the presence of the desired nucleic acid sequence. Typically, however, where there is only a minimal mismatch, (particularly when the mismatch is a 1-, 2- or 3-base mismatch or a 3-base deletion), there is some generation of "released fragments" even though the desired sequence is not present. Thus, the rate of generation of released fragments, and/or the final amount of released fragments, is quantified to indicate the presence or absence of the desired sequence. Such quantification is particularly useful when the determination further includes elucidation of a homozygous versus heterozygous state for the desired sequence in a diploid or polyploid organism. Such quantitation is also particularly useful for distinguishing between 1-base, 2-base and/or 3-base mismatches/deletions. Indeed, the quantitation may also distinguish between a nucleic acid probe that is wholly complementary to the selected nucleic acid molecule, and a nucleic acid probe that is fully complementary to the desired sequence, yet that has a mismatch in an adjacent sequence very near the desired sequence.

The perturbations in the rate of cleavage of the scissile linkage is also useful for the detection of triplet repeats, such as is found in Huntington's disease, and polymorphisms, such as HLA or T-cell receptor variance.

In other words, the detection of perturbations in the rate of generation of released fragments, and/or the total amount of released fragments generated, provides a powerful method for detecting minimal mismatches, as discussed above. Numerous methods of quantifying various labels, markers and other detectable materials are well known in the art, and can be readily applied to the instant invention by a person of ordinary skill in the art in light of the present disclosure.

In a particularly preferred embodiment, the method comprises performing two (or more) sets of reactions in different reaction vessels, wherein one of the reactions is performed using a nucleic acid probe that is complementary to the desired sequence for the selected nucleic acid molecule, and the second (or more) reactions is performed using a nucleic acid probe that is complementary to the suspected difference. Preferably, the desired sequence is identical to a native (or wild type) sequence, typically for a known gene.

This preferred embodiment is particularly useful for the positive determination of the presence of a mutation and the make-up of the mutation. For example, if the suspected difference is not present (e.g., there is no mutation), then the first reaction mixture containing the first nucleic acid probe (complementary to the desired sequence) will be positive, and the second reaction mixture containing the second nucleic acid probe (complementary to the suspected difference or mutation) will be negative. Conversely, if the suspected difference is present, then the first reaction mixture will be negative and the second will be positive. If there is a difference, but the difference is not the suspected difference, then both reaction mixtures will be negative. In such a case, it is possible to perform still further reactions directed to other suspected differences, and thereby elucidate the exact nature of the actual difference.

As used herein, excision, or cleavage, at the scissile linkage includes excision near the scissile linkage, provided such excision is initiated by the specific hybridization of the scissile linkage to the desired sequence. The one or more probe fragments that are released from the hybrid upon excision preferably include 5 or more nucleotides, but such fragments may be as small as a single nucleotide, provided the release of the single nucleotide is detectable (for example, where no detectable free nucleotides are initially included in the incubation mixture).

In one embodiment, the invention further provides a method that comprises repeating steps (a)–(c). In repeating these steps, the nucleic acid probe is present during incubation in an amount greater than, i.e., in molar excess over, the selected nucleic acid molecule. Thus, the selected nucleic acid molecule is allowed to cycle in what is known as a "cycling probe reaction." In such a reaction, if the nucleic acid probe is fully complementary to the selected nucleic acid sequence, then a single selected nucleic acid molecule repeatedly hybridizes with, and then releases from, numerous nucleic acid probes, thereby releasing numerous detectable probe fragments. Preferred embodiments of the cycling probe reaction are described in more detail below.

The nucleic acid probe may include an adjacent sequence-enzyme molecule located at one or both ends of the probe. Schematic illustrations involving such an adjacent sequence-enzyme molecule are provided in FIGS. 1–5. Such an adjacent sequence-enzyme molecule permits the excising agent to be bound to the nucleic acid probe when the reaction is initiated, thereby increasing the speed and efficiency of the method of present invention.

In one embodiment, the excising agent is present in a large molar excess. It is believed that such a large molar excess of the excising agent may permit the excising agent to bind to single-stranded nucleic acid probe (i.e., the excising agent binds prior to hybridization), thereby increasing the sensitivity of the method of the present invention. Where the excising agent is RNase H, the agent binds to the RNA portion of the single-stranded probe prior to hybridization. For example, the concentration of the excising agent may be up to about 4 µg/µl, or more, while the amount of the nucleic acid probe may be only about 0.001 pMoles. Preferably, the excising agent is present at a ratio of greater than about $10^6$ to 1 nucleic acid probe, more preferably at a ratio of greater than about $10^7$ to 1, yet more preferably at a ratio of greater than about $10^8$ to 1, and most preferably at a ratio of greater than about $10^9$ to 1. Within other embodiments of the invention, the quantity of probe will range from about 0.001 pMoles to about 10 pMoles, and the quantity of enzyme will range from about 2 µMoles to about 25 µMoles.

As noted above, the selected nucleic acid molecule is hybridized to a complementary nucleic acid probe having a scissile linkage. A wide variety of nucleic acid probes having scissile linkages may be utilized within the context of the present invention. The probe is designed such that, upon excision by an enzyme that is capable of specifically cleaving the probe-target complex at the scissile link, probe fragments are released that are detectable (see U.S. Pat. Nos. 4,876,187 and 5,011,769, discussed above, WO 89/09284 to Walder, published Oct. 5, 1989, and U.S. application Ser. No. 08/109,272, filed Aug. 18, 1993). The nucleic acid probe of this invention comprises the structure:

$(NA_1\text{-}SL\text{-}NA_2)_n$ wherein $NA_1$ and $NA_2$ are nucleic acid sequences (which may include peptide nucleic acids), wherein SL is the scissile linkage (typically comprising a nucleic acid sequence) that is able to specifically hybridize to or bind to the desired nucleic acid sequence and is able to be excised by an excising agent upon such hybridization or binding, thereby cleaving $NA_1$ from $NA_2$, and wherein n is an integer from about 1 to about 10.

It is an important feature of SL that its length is determined by the suspected difference between the selected nucleic acid molecule and the desired sequence. In particular, this means that SL must be of sufficient length to encompass the suspected difference, yet short enough that SL cannot inappropriately "specifically hybridize" to the selected nucleic acid molecule when the suspected difference is present; such inappropriate hybridization would permit excision (and cleavage) of SL even though the selected nucleic acid molecule was not fully complementary to the nucleic acid probe. Thus, in preferred embodiments, SL is between 3 to about 5 nucleotides in length, such that a suspected nucleotide difference from 1-nucleotide to 3-nucleotides is encompassed by SL, and 0, 1 or 2 nucleotides of SL are on either side of the suspected nucleotide difference.

In one embodiment of this invention, $NA_1$ and $NA_2$ in the nucleic acid probe independently comprise from about 0 to about 20 nucleotides or more and SL comprises from about 2 to about 100 nucleotides or more. In a preferred embodiment of this invention, $NA_1$ and $NA_2$ in the nucleic acid probe are DNA sequences and SL is an RNA sequence. In a further embodiment, $NA_1$ and $NA_2$ in the nucleic acid probe are RNA sequences and SL is a DNA sequence. In yet another embodiment, either $NA_1$ or $NA_2$ of the nucleic acid probe comprises either modified RNA or DNA, provided that SL retains the selective excision properties discussed above.

In one embodiment, excising the specifically hybridized SL sequence is carried out with a double-stranded ribonuclease that excises ribonucleic acid sequences from a double-stranded DNA-RNA hybrid. An example of such a ribonuclease is RNase H. As used herein, "excising" includes nicking or otherwise selectively disrupting the nucleic acid probe, at the specifically hybridized scissile linkage, regardless of whether one or more nucleotides are actually removed from the hybridized scissile linkage itself.

In the nucleic acid probes described above, where n is greater than one the unit $NA_1\text{-}SL\text{-}NA_2$ repeats. As will be readily understood by one having ordinary skill in the art, the unit may be the same within each repeat or it may vary randomly or in a defined pattern. The unit may vary in that $NA_1$, $NA_2$ or both may vary within each repeat, for example, by having different nucleic acid sequences from one repeat unit to the next. The variation may occur randomly such that in every repeat unit, $NA_1$ and $NA_2$, the sequence of bases is different, and may also vary in the number of bases of each of $NA_1$ and $NA_2$. An example of a random variation where n=3 and both $NA_1$ and $NA_2$ vary is:

$NA_1$-SL-$NA_2$-$NA_1$'-SL-$NA_2$'-$NA_1$"-SL-$NA_2$"

An example of a patterned variation where n=4 and both $NA_1$ and $NA_2$ vary is:

$NA_1$-SL-$NA_2$-$NA_1$'-SL-$NA_2$'-$NA_1$-SL-$NA_2$-$NA_1$'-SL-$NA_2$'

In both of the above examples, the solid lines joining each unit are chemical bonds that may be either hydrogen bonds or covalent bonds.

The $NA_1$-SL-$NA_2$ unit may also vary in the scissile linkage SL. For example, SL may vary where there is more than one desired sequence, or when the desired sequence encompasses suspected differences at more than one site. The variation in the sequence of nucleotides in SL will correspond to the variations in the desired sequences. Those skilled in this art will also readily appreciate that best results may be achieved with the use of nucleic acid probes whose lengths are relatively short, yet highly specific to the selected nucleic acid molecule. By decreasing rather than increasing the total number of nucleotides in the nucleic acid probe, high gain-low noise determination of the presence and/or amount of the desired sequence can be achieved.

Those skilled in this art will also readily appreciate that the total length of the nucleic acid probe may vary according to a number of factors including the nature of the desired sequence to be detected, the construction of the nucleic acid probe, e.g., whether the probe is a DNA-RNA hybrid or is constructed of RNA and modified RNA sequences alone, and so forth. It is important that the scissile linkage be accessible to excision in order that one or more nucleic acid probe fragments dissociate from the selected nucleic acid molecule. In this regard, it is preferable that the scissile linkage be located between nucleic acid sequences of from at about 8 to at least about 10 nucleotides, in order to facilitate denaturation of the probe fragments to become single-stranded upon excision and cleavage.

The nucleic acid probe of the present invention may have a detectable marker attached to, or encoded in, one or more of $NA_1$, $NA_2$, or SL. Such a marker may be any molecule or reagent that is capable of being detected. A multitude of such markers are well known in the art, including, for example, radioisotopes, radiolabeled molecules, fluorescent molecules, fluorescent antibodies, enzymes, chemiluminescent catalysts, and ligands capable of binding to specific proteins that have been tagged with an enzyme, fluorescent molecule or other detectable molecule. One example of a suitable ligand is biotin, which will bind to avidin or streptavidin. The nucleic acid probe (or the selected nucleic acid molecule) may also be immobilized on a solid support.

Methods for constructing such nucleic acid probes (and adjacent sequences that may be attached to $NA_1$ or $NA_2$), may be readily accomplished by one of ordinary skill in the art, given the disclosure provided herein. Preferred methods are described, for example, by the following: Matteucci and Caruthers, *J. Am. Chem. Soc.* 103:3185, 1981; Beaucage and Caruthers, *Tetrahedron Lett.* 22:1859–1862, 1981; U.S. Pat. Nos. 4,876,187 and 5,011,769; Ogilvie et al., *Proc. Natl. Acad. Sci. USA* 85:8783–8798, 1987; Usman et al., *J. Am. Chem. Soc.* 109:7845–7854, 1987; Wu et al., *Tetrahedron Lett.* 29:4249–4252, 1988; Chaix et al., *Nuc. Acids Res.* 17:7381–7393, 1989; Wu et al., *Nuc. Acids Res.* 17:3501–3517, 1989; Beaucage and Caruthers, *Tetrahedron Lett.* 22:1859–1862, 1981; McBride and Caruthers, *Tetrahedron Lett.* 24:245–248, 1983; Sinha et al., *Tetrahedron Lett.* 24:5843–5846, 1983; Sinha et al., *Nuc. Acids Res.* 12:4539–4557, 1984; and, Gasparutto et al., *Nuc. Acids Res.* 20:5159–5166, 1992.

Preferably, nucleic acid probe (and adjacent sequence) molecules are synthesized utilizing standard chemistries on automated, solid-phase synthesizers such as Applied Biosystems, Inc.'s Model 391 DNA Synthesizer (PCR-MATE EP) or Applied Biosystems, Inc.'s Model 394 DNA/RNA Synthesizer. Briefly, oligonucleotide synthesis is accomplished in cycles wherein each cycle extends the oligonucleotide by one nucleotide. Each cycle consists of four steps: (1) deprotecting the 5'-terminus of the nucleoside or oligonucleotide on the solid support, (2) coupling the next nucleoside phosphoramidite to the solid phase immobilized nucleotide, (3) capping the small percentage of the 5'-OH groups of the mobilized nucleotides which did not couple to the added phosphoramidite, and (4) oxidizing the oligonucleotide linkage to a phosphotriester linkage. Thus, within one embodiment of the invention, oligonucleotides may be synthesized essentially as follows. Briefly, a solid phase is selected whereby the first nucleoside is attached to the support by a base labile succinate linkage. The selection of the appropriate solid phase will depend upon the base at the sequence's 3'-terminus. The nucleoside attached to the 3'-terminus is deblocked to make available the 5'-OH for condensation with the next phosphoramidite. The dimethoxytrityl group that protects the 5'-OH of the immobilized nucleoside is removed by treatment with a di- or trichloroacetic acid solution. The next phosphoramidite is then added along with an activator, tetrazole, to couple the 5'-OH of the immobilized nucleoside to the added phosphoramidite and thereby forming a phosphite triester linkage. Any remaining uncoupled 5'-OH groups are then capped by the addition of an acetic anhydride solution, catalyzed by N-methyl imidazole. The capping of the uncoupled 5'-OH groups ensures that only oligonucleotides of a defined sequence will undergo further chain lengthening. The last step in the synthesis cycle is the oxidation of the phosphite triester linkage to the more stable and native phosphate triester linkage. The oxidation is accomplished by the addition of an aqueous iodine solution. The four steps of this synthesis cycle are then repeated until a chosen oligonucleotide sequence has been prepared.

Reagents for the synthesis of oligonucleotides for use as chimeric probes described above are commercially available from a variety of sources, including synthesizer manufacturers such as Applied Biosystems Inc. (Foster City, Calif.) and Millipore Corp. (Bedford, Mass.), as well as from Glen Research (Sterling, Va.) and Biogenex. For DNA synthesis, the preferred phosphoramidites are base labile phosphoramidites (such as N-base protected, cyanoethyl phosphoramidites) available from Applied Biosystems, Glen Research and Millipore Corp. For RNA synthesis, the preferred phosphoramidites are the base labile phosphoramidites (such as N-base protected, 2'-OH sugar protected, cyanoethyl phosphoramidites) available from Glen Research and Millipore Corp.

The result of the above synthesis is an N-base protected oligonucleotide phosphotriester immobilized on a solid support. In the case of RNA synthesis, in addition to the N-base protecting group, the immobilized phosphotriester is also 2'-OH protected. In order to prepare the chosen oligonucleotide, the modified form of the oligonucleotide should be cleaved from the solid support, the phosphodiester converted to the phosphodiester linkage native to DNA and RNA, and the bases N-deprotected. In addition, in the case of RNA synthesis, the 2'-OH group should also be deprotected.

Treatment of the solid support bearing the modified oligonucleotide with aqueous ammonia releases the 3'-OH group and cleaves the oligonucleotide from the solid support. The ammonia treatment also removes the cyanoethyl group of the phosphate triester to produce the desired phosphodiester. Within one embodiment of the invention, for a 0.2 μmole synthesis, the solid phase is treated successively with three portions of 0.8 ml each of freshly prepared 28%–30% aqueous ammonium hydroxide. The solid support is treated with each portion for 15 minutes at room temperature, and then the solutions are combined. The resulting ammonia solution contains an oligonucleotide in which its bases are N-protected, and in the case of RNA synthesis, the 2'-OH group also remains protected.

The labile N-base protecting groups may be removed from the oligonucleotides by allowing the above ammonia solution to stand overnight at room temperature. The overnight ammonia treatment will be effective only when base labile N-protecting groups are present in the original phosphoramidite synthesis reagent. The cyanoethyl phosphoramidites available from Applied Biosystems, Glen Research, and Millipore Corp. are preferred for this reason. In the case of DNA synthesis, the overnight treatment with ammonia yields a dideoxyoligonucleotide that is ready for purification and use. However, in the case of RNA synthesis, the overnight ammonia treatment yields a deoxyoligonucleotide in which the ribosilyl groups remain 2'-OH protected.

When the synthesized oligonucleotide includes one or more RNA bases, the 2'-OH ribosilyl protecting group (t-butyldimethylsilyl group) of the synthesized deoxyoligonucleotide is preferably removed after an initial purification of the oligonucleotide by high performance liquid chromatography (HPLC). In a typical application, the above described ammonia solution containing the 2'-OH protected deoxyoligonucleotide is concentrated to dryness. The RNA residue is dissolved in 100 μl of 10% buffer B (95% acetonitrile in 100 mM triethylammonium acetate) and 90% buffer A (5% acetonitrile in 100 mM triethylammonium acetate). The resulting solution is centrifuged at 14,000 RPM and the supernatant withdrawn. The solution is then ready for HPLC purification. The oligonucleotide may be purified on a Millipore HPLC Waters 600E Control System using a Millipore Delta Pak (5μ C18 300A, 3.9×150 mm) Analytical Column eluting with buffers A and B, as described above, operating in a linear gradient mode (10% to 61% B, 10% B for the first 5 minutes then increasing to 61% B during the following 17 minutes). The product elutes at approximately 50% B. The fractions containing purified product may then be pooled and transferred to two 2 ml tubes to be evaporated to dryness. The resulting HPLC purified 2'-OH protected deoxyoligonucleotide may then be deprotected.

The t-butyldimethylsilyl 2'-OH ribosilyl protecting groups may be removed by treatment with a fluoride solution. Briefly, within one embodiment, to each of the two tubes was added 0.25 ml of 1.0M tetrabutyl ammonium fluoride in tetrahydrofuran (Aldrich Chemical Co., Milwaukee, Wis.). The solutions are allowed to stand overnight at room temperature after which 1.75 to 2.0 ml water is added to each tube. The fully deprotected synthetic RNA may be isolated by size exclusion chromatography. More specifically, for the above preparation four NAP 10 Sephadex G-25 columns (Pharmacia Corp., Piscataway, N.J.) are prepared according to the manufacturer's instructions. One milliliter of the above RNA-containing solution is applied to each column. Each column is then eluted with 1.5 ml distilled water, and the eluant collected, combined, and evaporated to dryness. The resulting solid is dissolved in 100 μl buffer A (described above) and centrifuged at 14,000 RPM for 5 minutes. The supernatant solution containing the size exclusion purified RNA containing solution is collected and HPLC purified as described above, except that the linear gradient is 0 to 15% B (15% B at 30 minutes). The fully deprotected RNA elutes at about 11% B. The product fractions are then collected, pooled, and evaporated. The yield of the fully deprotected RNA containing product may be quantitated by measuring the absorbance at 260 nm.

CONSTRUCTION OF OLIGONUCLEOTIDE-ENZYME MOLECULES

As noted above, the present invention also provides oligonucleotide-enzyme molecules, such as an adjacent sequence-enzyme molecule, comprising an enzyme capable of cleaving scissile linkages, and a single stranded nucleic acid (e.g., DNA, RNA) molecule. Such a molecule may have the excising agent attached to, or tethered to, the nucleotide sequence $NA_1$ and/or $NA_2$. Briefly, in one embodiment, the adjacent sequence-enzyme molecule is selected such that it is both complementary to the selected nucleic acid molecule, and near the hybridization site (scissile linkage) of the nucleic acid probe. When more than one adjacent sequence-enzyme molecule is used, the second adjacent sequence-enzyme molecule is preferably selected such that it is complementary to the selected nucleic acid molecule and is positioned at an opposing end of the nucleic acid relative to the first adjacent sequence-enzyme molecule.

Such fusion molecules may be constructed by a variety of methods, including but not limited to those described above relating to the production of oligonucleotides. For example, the nucleic acid probe may be modified at either the 5'- or the 3'-terminus with a suitable reactive functional group. Alternatively, a reactive functional group may be incorporated into interior positions of the nucleic acid probe. Suitable reactive functional groups for use within the present invention include nucleophilic groups such as primary amino and thiol groups. These groups may be readily incorporated into the nucleic acid probe during the automated synthesis of the nucleic acid probe. For example, using AMINOLINK 2 (Applied Biosystems Inc., Foster City, Calif., part no. 400803, ABI User Bulletin No. 49) as a reagent in the automated synthesis of the nucleic acid probe (PCR-MATE EP Model 391 DNA Synthesizer, ABI, Foster City, Calif.), a primary amino group may be covalently attached during the final coupling cycle to the 5'-terminus of the synthetic oligonucleotide comprising the nucleic acid probe. Cleavage from the solid support and purification by high pressure liquid chromatography provides an amino-modified synthetic oligonucleotide suitable for coupling to a variety of other molecules such as those mentioned above. Utilizing similar reagents and methodologies, 3'-amino, as well as 5'- and 3'-thiol, modified oligonucleotides may be prepared.

To effect the coupling (preferably covalent) of the oligonucleotide to another molecule (i.e., the excising agent), the other molecule should be suitably reactive, that is, capable of forming a covalent bond with the reactive functional group on the oligonucleotide. Typically for amino-modified oligonucleotides, their coupling partners bear a reactive carboxylic acid derivative, which results in the formation of an amide link between the oligonucleotide and the other molecule. Many varieties of reactive carboxylic acid derivatives are suitable for coupling. Suitable reactive groups include activated esters such as n-hydroxysuccinimide derivatives, mixed anhydrides, and acid halides. Preferred carboxylic reactive groups include N-hydroxysuccinimide esters. For example, carboxylic derivatives of biotin and fluorescein, a widely used fluorescent dye, are commercially available from many sources and are routinely used to label amino-modified oligonucleotides as well as other biological molecules which bear reactive amino groups. Biotin and fluorescein ammidites, N-hydroxysuccinimide esters of biotin and fluorescein are commercially available.

In the present invention, a suitable tether may be covalently attached to the amino-modified oligonucleotide to facilitate attachment to and function of the excising agent of (e.g., RNase H). The tether should be flexible and sufficiently long to allow the active site of the enzyme to reach and act upon the substrate, the scissile portion of the oligonucleotide probe. Additionally, the tether should be bifunctional with regard to its reactivity such that the tether may form a covalent bond with the oligonucleotide and the enzyme. Suitable tethers may include heterobifunctional agents that are designed for protein coupling and modifications. See, e.g., Means and Feeney, *Chemical Modification of Proteins*, Holden-Day, 1971. As utilized herein, the term "heterobifunctional" refers to the fact that the agent bears two reactive functional groups as coupling sites, that the coupling sites are different from each other and therefore capable of selective coupling to two different binding partners, for instance, an amino-modified oligonucleotide and a thiol-modified excising agent. Suitable tethers include commercially available heterobifunctional coupling agents such as succinimidyl 4-(N-maleimidomethyl)cyclohexane-1-carboxylate, "SMCC" (Pierce Chemical Co., Rockford, Ill., part no. 22320 H). Briefly, SMCC bears an N-hydroxysuccinimide group that, when reacted with an amine such as an amino-modified oligonucleotide, forms an amide linkage between the oligonucleotide and the tether. SMCC also bears an N-methylmaleimide group that is selectively reactive toward thiol groups. The length and flexibility of the SMCC tether is defined by the cyclohexane moiety that spans the two reactive groups. One skilled in the art may vary the moiety that spans the two reactive groups to achieve the flexibility and length necessary for improved function of the probe of the present invention. Accordingly, reaction of the amino-modified oligonucleotide with SMCC produces a tethered oligonucleotide that, by virtue of the N-methyl maleimide group, is capable of further tethering to a second molecule suitably functionalized with a thiol group.

Once the tethered oligonucleotide bearing the N-methylmaleimide functional group is synthesized, reaction with any thiol-bearing molecule will result in the covalent attachment of the tethered oligonucleotide to the thiol-bearing molecule through the formation of a carbon-sulfur covalent bond. In the present invention, the thiol-bearing molecule is the excising agent of interest, which excising agent typically bears a single reactive thiol group, a cysteine residue. Alternatively, for those molecules that do not contain thiol groups, thiol groups may be incorporated into these molecules by standard chemical methods. See, e.g., Means and Feany, supra. Therefore, reaction of the tethered oligonucleotide with the excising agent results in covalent bond formation between the enzyme thiol and the tether maleimide, and provides the tethered enzyme-nucleic acid probe of the present invention. The probe thus produced is a 1:1 complex of enzyme to oligonucleotide in which the enzyme and oligonucleotide are spatially separated by the tether.

Single-Stranded Nucleic Acid Binding Proteins

In one embodiment, the present invention includes the use of a single-stranded nucleic acid or DNA binding protein (SSB), which protein enhances the efficiency of the hybridization and the denaturation of the probe and the target nucleic acid molecule. Examples of SSBs suitable for use in the present invention include *E. coli* SSB (EcoSSB), T4 gene 32 protein (SSB32) (Chase J. W. and Williams, K. R., *Ann. Rev. Biochem.* 55:103, 1986), T7 SSB, Coliphage N4 SSB, calf thymus unwinding protein and adenovirus DNA binding protein (Coleman et al., *CRC Critical Rev. Biochem.* 7:247, 1980; Lindberg et al., *J. Biol. Chem.* 264:12700, 1989; Nakashima et al., *FEBS Lett.* 43:125, 1974). It is believed SSBs function by decreasing or removing secondary structure in ssDNA (Munuyappa et al., *Proc. Natl. Acad. Sci. USA* 81:2257–2261 (1984). EcoSSB is stable up to 100° C. (Weiner, J. H. et al., *J. Biol. Chem.* 250:1972–1980, 1975), and has been found to be less sensitive to salt concentrations than SSB32. EcoSSB also has a lower tendency to aggregate than SSB32 (Chase J. W. and Williams, K. R., *Ann. Rev. Biochem.* 55:103–136, 1986).

EcoSSB, SSB32 and phage T7 SSB improve hybridization of polynucleotides with complementary nucleic acid sequences (WO 9106679, published May 16, 1991). SSB32 has been found to improve the direct sequencing of λ DNA from crude cleared lysates or plate lysates without purification of the bacteriophage particles by Cesium Chloride centrifugation (Lasham, A. and Darlison, M. G., *Mol. Cell Probes* 7:67–73, 1993). SSB32 is also useful for improving the specificity of hybridization, and can be used with mispairing for the identification of point mutations. EcoSSB reduces artifacts during deletion mutagenesis when used with Taq DNA polymerase (Chou, Q. *Nucleic Acids Res.* 20:4371, 1992).

Thus, in one embodiment, the present invention includes a method of enhancing the ability of cycling chimeric probes to detect pairing (or lack of pairing) between a probe and a target (i.e., a desired nucleic acid molecule) by the addition of SSBs to the reaction mixture in order to increase stable pairing and lower the melting temperature of the mismatched hybrid, thereby enhancing the difference in the rate of cleavage between the mismatched target and the perfectly matched target.

Biotin—Streptavidin linkages

Within a further embodiment of the invention, the nucleic acid probe may be biotinylated in order to facilitate binding to an avidinated or streptavidinated enzyme. Within a preferred embodiment of the invention, the nucleic acid probe is bound to RNase H through a streptavidin-biotin linkage.

Briefly, biotinylated oligonucleotides may be prepared by the covalent coupling of a reactive form of biotin (typically, an N-hydroxysuccinimide ester) with a suitably reactive oligonucleotide (typically, a 5'-amino modified oligonucleotide prepared by coupling a suitable amino containing phosphoramidite, i.e., from Applied Biosystems Inc., in the last step of an automated, solid-phase oligonucleotide synthesis). Alternatively, the biotinylated probe may be prepared directly by using a biotin phosphoramidite during the automated, solid-phase synthesis of the oligonucleotide probe.

Suitable biotin phosphoramidite reagents are commercially available. For example, biotin phosphoramidite and biotin-dT (also a phosphoramidite), are available from Glen Research and are specifically designed for automated oligonucleotide synthesis. The former reagent is useful for incorporating a functional biotin at either the 3'- or 5'-terminus of an oligonucleotide, while the latter may be used to incorporate biotin into the oligonucleotide at any position within the oligonucleotide.

Streptavidin-enzyme molecules may also readily be constructed given the disclosure provided herein. A particularly preferred streptavidin—RNase H fusion molecule is set forth in more detail below in Example 2.

In a further aspect, the present invention provides a method of determining whether a selected nucleic acid molecule differs from a native nucleotide sequence, comprising the following steps: (a) incubating the selected nucleic acid molecule with a nucleic acid probe as described above, under conditions suitable for specific hybridization of the selected nucleic acid molecule with the nucleic acid probe to produce a hybrid; (b) contacting the hybrid with an excising agent capable of cleaving the nucleic acid probe at its scissile linkage when the nucleic acid probe is specifically hybridized at the scissile linkage to the selected nucleic acid molecule, thereby releasing one or more fragments of the nucleic acid probe from the hybrid; and (c) detecting the released fragments and therefrom determining whether the selected nucleic acid molecule differs from the native nucleotide sequence.

It is a feature of this aspect of the invention that the method readily detects a somatic mutation at a site where the scissile linkage of the nucleic acid probe is capable of hybridization. The detection of a somatic mutation is particularly useful where the selected nucleic acid molecule is derived from an oncogene. This aspect of the invention also readily detects a germ mutation at a site where the scissile linkage of the nucleic acid probe is capable of hybridization.

In another aspect, the present invention provides a method of determining whether a selected nucleic acid molecule tends to induce cystic fibrosis. In this aspect, the method comprises the following steps: (a) incubating the selected nucleic acid molecule with a nucleic acid probe as described above, the nucleic acid probe complementary at its scissile linkage to a native nucleotide sequence for the transmembrane conductance regulator gene at a site in the gene susceptible to a mutation tending to induce cystic fibrosis, under conditions suitable for hybridization of the selected nucleic acid molecule with the nucleic acid probe to produce a hybrid; (b) contacting the hybrid with an excising agent capable of cleaving the nucleic acid probe at its scissile linkage when the nucleic acid probe is specifically hybridized at the scissile linkage to the selected nucleic acid molecule, thereby releasing one or more fragments of the nucleic acid probe from the hybrid; and (c) detecting and quantitating the released fragments, and therefrom determining whether the selected nucleic acid molecule differs from the native nucleotide sequence, which indicates that the selected nucleic acid molecule tends to induce cystic fibrosis.

In alternative embodiments, the methods of the present invention detect mutations, typically single-base mutations, that tend to induce cancer. Such mutations may be found in the HER/neu2 gene (Tal et al., *Mol. and Cell. Biol.* 7:2597, 1987), the Ras gene, which typically has a mutation in codon 12, 13 or 61 (Kumar et al., *Science* 248:1101–04, 1990) or the p53 gene, which has four "hot spots" that coincide with four highly conserved regions of the gene (Nigro et al., *Nature* 342:705–08, 1989). Further, the methods can detect mutations, typically single-base mismatches or single-codon deletions, that are inherited. Examples of such mutations include those to the hemoglobin genes, which are implicated in sickle cell anemia and some thalessemias, and the genes coding for the components of the hemostatic mechanism, or clotting, which are implicated in various hemophilias (Beckman et al., *Nelson Textbook of Pediatrics*, pp. 1242–48, 1983).

It is a feature of this aspect of the present invention that the method may be applied to a selected nucleic acid molecule derived from diploid animal and that the method can distinguish whether the animal is (a) homozygous for a mutation(s) tending to induce cystic fibrosis, (b) heterozygous for a mutation(s) tending to induce cystic fibrosis and native nucleotide sequence, or (c) homozygous for a native nucleotide sequence. Of course, the other aspects of the method of the present invention can also distinguish between such heterozygous and homozygous states in a diploid (or polyploid) organism with respect to other mutations, including mutations in other genes. Therefore, all aspects of the present invention specifically include determinations of homogeneity or heterogeneity of a mutation or other difference between a selected nucleic acid molecule and a desired sequence.

Exemplary Reaction Conditions Suitable for Carrying out the Present Invention

The selected nucleic acid molecule and the nucleic acid probe, which probe is typically present in excess relative to the selected nucleic acid molecule, are combined under conditions suitable for specific hybridization of the selected nucleic acid molecule and the desired sequence. Such conditions include a reaction mixture with an appropriate buffer. In one embodiment, the buffer contains 8 to 10 mM $MgCl_2$ and 40 to 50 mM Tris-HCL pH 7.5 to 8.1 and 0.025% Triton X 100. Such hybridization conditions, including appropriate reaction mixtures and buffers, are well known in the art. The reaction mixture so formed is incubated at a suitable temperature typically from about 60° C. to about 70° C., and preferably at about 65° C. for from about 5 minutes to about 30 minutes, although the time period may extend up to about 60 minutes or longer to produce more fragments.

The reaction mixture, which includes the potentially specifically hybridized nucleic acid probe and selected nucleic acid molecule, also includes an excising agent under such conditions. The inclusion of the excising agent may require additional time in order for hybridization, excision, and denaturation to occur. The additional amount of time may vary from about 1 to about 60 minutes, although about 30 minutes is sufficient in most cases. The cycling reaction that occurs in the presence of excess nucleic acid probe may take place in a short period of time, typically milliseconds, or less.

Excising the double-stranded selected nucleic acid molecule-nucleic acid probe hybrid at least once within the scissile link leaves at least one probe fragment momentarily hybridized to the selected nucleic acid molecule. However, this probe fragment denatures from the hybrid as the result of the change in length of the hybridized nucleic acid probe sequences in the hybrid. For example, a nucleic acid probe having an initial length of 25 nucleotides (i.e., a 25-mer) will hybridize, and remain hybridize, to a complementary nucleic acid and molecule (i.e., the selected nucleic acid molecule) under the incubation condition at 65° C. After excision, however, where the scissile link is a nucleotide base sequence between two 8-nucleotide base sequences, the remaining two 8-mer hybridized probe fragments will denature (i.e., melt or fall off) the hybrid. These single-stranded probe fragments may then be identified using well-known methods, thereby detecting the selected nucleic acid molecule.

A-T and G-C base pairs exhibit variation in melting or denaturation temperature ($T_m$s) of approximately 2°/base pair and 4°/base pair for short oligomers, respectively. Thus, on average, assuming equal ratios of A-T and G-C base pairs in a hybridized target-probe complex, each paired nucleotide in a hybrid exhibits a melting point variation of approximately 3°/base pair.

Detecting and quantifying the probe fragments, and thereby performing the determination of step (c), may be performed using a number of methods well known in the art. The method of detection in step (c) will depend on the type of label or detectable marker, as discussed above. For example, detection of the nucleic acid probe may be performed by coupling to a radioisotopic or fluorescent label, or by ATP generation. The results of the reaction may then run on an acrylamide gel, thereby separating cleaved nucleic acid probe (i.e., probe fragments) from uncleaved nucleic acid probe. In one embodiment, where the scissile linkage is constructed of ribonucleic acid (RNA), the results of the cleaving step will include monoribonucleotides to short oligoribonucleotides. Such oligoribonucleotide fragments will possess unique 5' phosphate groups that may be advantageously used in their detection. Among such fragments are 5'-adenosine monophosphates (5'-AMP), which may be fed into an enzymatic ATP generating system and subsequently linked to a luciferin-luciferase photometric read out system. Further, the proximal segment will have a 3'-OH terminus. These termini can be tailed with a suitable polymerase such as polynucleotide phosphorylase or poly A polymerase, and thereby be detected and quantitated, or used in a subsequent reaction. As an alternative method of detection and quantitation, the generated probe fragments may be detected and quantitated using high performance liquid chromatography (HPLC).

In the embodiment where hybridization is carried out with the typical excess of probe and in the presence of a suitable excising agent, such as RNase H, the method of the present invention can cycle, thereby repeating steps (a)–(c) and generating numerous probe fragments (see FIGS. 1–6). In such an embodiment, the probe can hybridize, be cleaved and denature under constant incubation conditions, such as the 65° C. example discussed above. High gain-first stage detection of $10^{-23}$ moles of selected nucleic acid molecule with a radioisotope label may be obtained.

The following examples are offered by way of illustration, and not by way of limitation.

EXAMPLE 1

CONSTRUCTION OF NUCLEIC ACID PROBES

Nucleic acid probe molecules useful in the methods of the present invention have been constructed on a solid support medium (either silica gel or controlled pore glass) using either a hydrolysable linkage or a permanent (non-hydrolysable) linkage. Published chemical methods were used for this synthesis. Nucleic acid probe molecules are constructed as generally described by Matteucci and Caruthers, *J. Am. Chem. Soc.* 103:3185, 1981; Beaucage and Caruthers, *Tetrahedron Lett.* 22:1859, 1981; (Alvarado-Urbina et al., "Automated Synthesis of Gene Fragments," *Science* 214:270–274, 1981; Van Boom and Wreesman, "Chemical Synthesis of Small Oligoribonucleotides in Solution," *In Oligonucleotide Synthesis—A Practical Approach*, IRL Press, Gait (ed.), pp. 153–183, 1984; see also U.S. Pat. Nos. 4,876,187 and 5,011,769. In particular, oligonucleotides are synthesized on an Applied Biosystem Inc. Model 391 DNA Synthesizer (PCR-MATE-EP*) utilizing protocols described by the manufacturer, and CE-phosphoramidite reagents from Glen Research (Sterling, Va.).

Utilizing this procedure, the following oligomers are synthesized (capital letters have been utilized to denote deoxyribonucleotides, and lower case letters have been utilized to denote ribonucleotides):

Probe Sequence (SEQ. ID. NO.: 1) 5'-CAT CAC Cgg aaT TGA AGC C-3'
Probe Target Sequence (SEQ. ID. NO.: 2) 5'-GGC TTC AAT TCC GGT GAT G-3'
Distal Flanking Sequence Probe (SEQ. ID. NO.: 3) 5'-TTG CTC GGT GAT GCC CAG CGC CGA ATT C-3'
Distal Flanking Sequence Target, (SEQ. ID. NO.: 4) 5'-GAA TTC GGC GCT GGG CAT CAC CGA GCA A-3'
Proximal Flanking Sequence Probe (SEQ. ID. NO.: 5) 5'-CGT CGG GCG CAG CCC ACG GGA CGC GGC AGG-3'
Proximal Flanking Sequence Target (SEQ. ID. NO.: 6) 5'-CCT GCC GCG TCC CGT GGG CTG CGC CCG ACG-3'

EXAMPLE 2

CONSTRUCTION OF A NUCLEIC ACID PROBE CONTAINING STREPTAVIDIN-RNASE H

A. Construction of Streptavidin-RNase H fusion protein

1. Construction of pIDB1

Genomic DNA from *T. thermophilus* (ATCC No. 27634) is amplified by PCR utilizing primers BC202 and BC203 (Table 1 below), and cloned as blunt end fragments into the Sma I site of pTZ19R (Pharmacia, Piscataway, N.J.). The resultant plasmid is designated pIDB 1.

2. Construction of pIDB2

A fragment from pIDB1 is amplified utilizing primers BC214 and BC202 (see Table 1 below), and cloned into the Sma I site of pTZ19R as a blunt end fragment. This plasmid is designated pIDB2b. The EcoR I fragment of pBI-730b is cloned into pT7-7 (Dr. Stan Tabor, Harvard Medical School, Boston, Mass.). The resultant plasmid is designated pIDB2.

3. Construction of (pBI-759) pIDB9

In order to obtain the RNase H gene expressed in its native form, primers FB102 and BC202 (see Table 1 below) were utilized to simplify the corresponding fragment from pIDB 1, and clone it as a blunt end fragment into the Sma I site of pTZ19R. The resultant plasmid is designated pBI-756. The restriction fragment Nde I-EcoR I from pBI-756 is then cloned into pT7-7 to generate pIDB9. This plasmid contains the RNase gene expressed in its native form.

4. Construction of pIDB10: a Streptavidin-RNase H fusion protein

The sequence encoding RNase H is first PCR amplified from pIDB1 utilizing primers FB102 and BC202 (Table 1). The amplified fragment is kinased and ligated into the vector pTSA-18F that has been previously cut with Sma I and treated with phosphatase. The vector pTSA-18F (Sano and Cantor, B. B. R. C. 176:571–577, 1991; U.S. Pat. No. 4,839,293), contains a DNA fragment coding for a truncated form of streptavidin, which is controlled by the T7 promoter. The resultant plasmid is designated pIDB 10.

pIDB10 expresses a streptavidin-RNase H fusion protein that is 291 amino acids in length. In particular, pIDB10 encodes amino acid residues 16 to 133 of the mature streptavidin at the N-terminus in-frame with amino acids 1 to 165 of *T. th.* RNase H. The streptavidin-RNase H junction of pIDB 10 is continued by determining the DNA sequence.

5. Construcaon of pIDB 11: a Streptavidin-RNase H fusion protein

The sequence encoding RNase H is first PCR amplified from pBI-730 utilizing primers FB106 and FB107, cut with EcoR I and HindIII and cloned into the same sites in pTSA-18F. This plasmid is designated pIDB11. This plasmid expresses a streptavidin-RNase H fusion protein which is 287 amino acids in length.

TABLE 1

| Designation | SEQ. I.D. No. | Seguence 5' to 3' |
|---|---|---|
| BC202 | 7 | CCG AAT TCT TAT GCC TCT TCG TGA |
| BC203 | 8 | CCG AAT TCA ACC CCT CCC CCA GGA |
| BC214 | 9 | CCG AAT TCC CTC CCC CAG GAA AC |
| FB102 | 10 | CCG CAT ATG AAC CCC TCC CCC AGG |
| FB106 | 11 | AAG GTG AAT TCA ATG AAC CCC TCC CCC AGG |
| FB107 | 12 | ACC AAG CTT CTT ATG CCT CTT CGT GAA |

B. Expression and Purification pDB10 and pDB11 are transfected into the bacterial strain NM522 (Gough and Murray, *J. Mol. Bid.* 166:1–19, 1983). Expression of the fusion gene is controlled by the T7 promoter. T7 RNA polymerase is supplied by infecting the transformed strains with an M13 phage containing the T7 polymerase gene under control of the lac UV5 promoter (Studier and Moffatt, *J. MoL Biol.* 189:113–130, 1986; Studier et al., *Meth. Enzymol.*, 185:60–89, 1990).

The streptavidin-RNase H fusion protein is purified from transformed NM522 containing pIDB10 or pIDB11 essentially as described below. Briefly, NM522 cells containing pIDB10 and pIDB11 is grown at 37° C. in 1 L of 2×YT medium (2×YT=10 g yeast extract, 16 g Bacto-tryptone, 5 g NaCl per liter, pH 7.0) containing 0.05 mg/ml ampicillin overnight. When the culture has reached an O.D.$_{600}$ of 0.3, IPTG is added to a final concentration of 0.3 mM in order to induce the lac operon. After 30 min., 15–30 mL of M13 phage (approximately 5×10$^9$ pfu/ml) containing the T7 RNA polymerase gene is added to initiate transcription of the fusion gene. The cells are then grown for an additional 3–4 hours before harvest.

Cells are harvested by centrifugation at 2900×g for 15 min. at 4° C. Cell pellets are resuspended in 30 mL of lysis buffer (1M Tris, pH 7.4, 1 mM EDTA), and stored frozen at −70° C. After thawing, cells are lysed using a French press and centrifuged at 39000×g for 15 min. at 4° C. The pellet is resuspended in Urea buffer (20 mM sodium acetate, pH 5.5, 8M urea), and homogenized using a 20.5 gauge needle and syringe. The sample is again clarified by centrifugation at 39000×g for 15 min. The protein solution is applied to a 2 mL phosphocellulose (Sigma) column connected to an FPLC system (Pharmacia, Piscataway, N.J.), which has been equilibrated with Urea buffer. The column is washed with 8M urea, 0.2M NaCl and the protein is eluted using a 0.2 to 0.7M NaCl linear gradient in 8M urea, 20 mM NaOAc, pH 5.5. Fractions are pooled and dialyzed overnight without stirring in 0.2M ammonium acetate, pH 6.0, 0.1 mM EDTA, and 0.02% NaN$_3$.

The fractions are dialyzed briefly against loading buffer (1M NaCl, 50 mM sodium carbonate, pH 10.5), then centrifuged at 39,000×g for 15 minutes. The sample is then applied to a 1.2×1.5 2-iminobiotin-agarose column Sigma Chemical Co., St. Louis, Mo., (pre-equilibrated with loading buffer) (Sigma). The column is washed with loading buffer, and the protein eluted with 6M urea, 50 mM ammonium acetate pH 4.0, and 0.1 mM EDTA. The eluted protein fractions are pooled, and applied to a PD-10 (Pharmacia, Piscataway, N.J.) desalting column equilibrated with 10 mM sodium acetate pH 5.5, and 150 mM NaCl. Protein which elutes from the desalting column is concentrated with a Centficon 10 filter (Amicon). The concentration of protein is determined by spectroscopy ($A_{280}^{0.1\%}$=2.3 for) pIDB10 and pIDB11 with a molecular mass of 31,742 and 31,139, respectively). Purity is analyzed by SDS-PAGE.

C. Determination of Streptavidin Activity

The activity of streptavidin may be determined by a modified ELISA assay. For example, varying amounts (i.e., 5, 50 and 500 n(μ)g) of fusion protein in Phosphate Buffered Saline ("PBS"), pH 7.0, is coated in duplicate into each well of a microtiter plate for 2 hours. Unbound protein is washed out with TBST buffer (50 mM Tris-HCl pH 7.9, 150 mM NaCl, 0.05% Tween 20), and 50 ng biotin-conjugated alkaline phosphatase (Sigma Chemical Co., St. Louis, Mo.) is added. After 60 minutes, p-nitrophenyl phosphate (1 mg/ml) was added to detect alkaline phosphatase activity.

D. RNase H Assay

The activity of RNase H may be measured using either the acid soluble counts method, or the cycling probe technique (CPT, Duck et al 1990; Cloney, et al., *Clinical Chem.* 404:656, 1994; see Example 5).

The acid soluble counts assay is based on a previously published method (Dirksen and Crouch, *J. Biol. Chem.* 256:11569–11573, 1981). Briefly, a reaction mix containing 10 mM Tris, pH 9.0, 10 mM MgCl$_2$, 50 μg BSA and 1–3 μM $^3$H-UTP labeled M13 (Kane, *Biochem* 27:3187–3191, 1988) is added to 1 μl enzyme (0.1–0.02 ng). The reaction proceeds for 5–10 min., then the reaction is stopped by the addition of 50 μl of 0.5 mg/ml carrier tRNA and 150 μl of 20% TCA. The reaction mix is then placed on ice for 5–10 min. Samples are centrifuged at 15,000 g for 5 min. at 4° C. 50 μl of the supernatant is added to 5 ml of liquid scintillation fluid. The acid soluble fraction is calculated according to the formula (counts-background)×4/(time(min.)×49×10$^6$). 49×10$^6$ dpm corresponds to 1 nmole of substrate.

RNase H activity with M13DNA:RNA substrate

The RNase H activity of the fusion (pIDB10, pIDB11) was compared to the activity of the native RNase H (pIDB9). The results show that the native enzyme has approximately 8 fold greater activity than the fusion enzyme pIDB10. A preliminary experiment showed that the fusion enzyme pIDB10 is slightly more active than the fusion enzyme pIDB11 (results not included). A temperature study was performed to compare the fusion enzyme pIDB10 to the native enzyme pIDB9 The enzymes were diluted in glycerol buffer (40% glycerol, sodium acetate 20 mM, pH 5.5, sodium chloride 150 mM) and subjected to different temperatures. The native enzyme is more stable than the fusion enzyme, but the fusion enzyme is still active after a 10 min. heat treatment at 60% activity relative to the control without heat treatment.

EXAMPLE 3

ATTACHMENT AND PURIFICATION OF A BIOTINYLATED NUCLEIC ACID PROBE INCLUDING AN ADJACENT SEQUENCE STREPTAVIDIN-RNASE H MOLECULE

Streptavidin-RNase H and the biotinylated oligonucleotide probe are mixed at a ratio of 1:5 (molar ratio of enzyme to probe). The sample is then separated by High Pressure Liquid Chromatography (HPLC) on a NucleoPac PA 100 column (Dionex Corp., Sunnyvale, Calif.), utilizing a gradient of 100% Eluent 1 (20 mM Phosphate, pH 6.0) to 100% Eluent 2 (20 mM Phosphate/1.0M NaCl, pH 6.0), at a flow rate of 1.5 ml/min.

EXAMPLE 4

USE OF ADJACENT SEQUENCE-ENZYME MOLECULES AND NUCLEIC ACID PROBE IN A CYCLING PROBE REACTION

A. Radioactive labeling of probe

The reaction probe is prepared by the addition of a radioactive $^{32}$P label to the 5' end of the oligonucleotide probe (Sambrook et al, 1990). Briefly, approximately 5 pmoles of the probe is labeled with 25 μL of [$^{32}$P], ATP (6000 Ci/mmol) in a robe containing T4 polynucleotide kinase ("Ready to Go" Pharmacia cat. No. 27-0736-02) in a final volume of 50 μL and the reaction is incubated at 37° C. for 0.5 hour. Subsequently, 4 μL of 0.5M EDTA, pH 8.0 is added, and the reaction is further incubated at 90° C. for 5 minutes.

Labeled probe is separated from unincorporated label on 2×1 mL Sephadex G-50 column or 1×Chromaspin-10 column (Clontech PT1300-1). The reaction mixture is first diluted to 100 μl with distilled water and then applied to the column. The reaction mixture is washed into the column with 400 μL of water. The labeled probe is then eluted with 400 μL of water, dried in a vacuum evaporator.

B. Cycling reaction

Reaction robes are set up in a final volume of 10 μl cycling buffer (40 mM Tris, pH 8.1, 8 mM MgCl$_2$, 0.025% Triton-X 100), containing 1 μl of target DNA (single or double stranded) sample, or with no DNA as a control, 1 μl (1 fmole) of labeled probe (or RNase H covalently linked to the probe, or fusion RNase H bound to biotinylated probe), 1 μl of the RNase H (0.1 μg @ 5000 fmole, or the adjacent oligonucleotide covalently linked to RNase H or the biotinylated adjacent oligonucleotide bound to fusion RNase H. An initial step is required for the use of fusion streptavidin-RNase H prior to the CPT reaction. The binding of fusion enzyme to biotinylated oligonucleotide probe or adjacent oligonucleotide is carried out for 15 min. using the cycling buffer supplemented with 1.0M NaCl. The robes are incubated for 30 minutes at 65° C., a temperature that allows efficient hybridization of the full-length probe (or adjacent oligonucleotides) to target (or adjacent to target) DNA sequences, but is above the $T_m$ of the duplex containing nicked probe, such that nicked probe melts off. Digested probe accumulates as RNase H and nucleic acid target catalyze the cleavage of the labeled probe. The target sequence remains intact and becomes available for further hybridization with uncleaved probe.

Following incubation, 10 μL of a dye mixture containing 10M urea, 0.01% bromophenol blue ("BPB"), 0.01% xylene cyanol and 50 mM EDTA is added to each reaction. Samples are then heated to 90° C. for 5 minutes to ensure denaturation, loaded onto a 7M urea-20% acrylamide/bis-acrylamide (19:1) gel, and electrophoresed at 450–600 volts.

The gel is analyzed on a PHOSPHORIMAGER™ utilizing IMAGEQUANT™ software (Molecular Dynamics, Sunnyvale, Calif.).

EXAMPLE 5

DETECTION OF 1-, 2-, AND 3-BASE MISMATCHES

Using the oligonucleotide preparation procedure described above, the following selected nucleic acid probe and selected nucleic acid sequences were produced:

Nucleic acid probe

ARK-2: 5'GTC GTC AGA CCC aaaa CCC CGA GAG GG3' (Seq. I.D. No. 13)

Selected nucleic acid sequences:

Wild Type:

ARK-2T: 5'CCC TCT CGG GG TTTT GGG TCT GAC GAC3' (Seq. I.D. No. 14) (Lanes 3 & 8 ("cont$^{10}$") in FIG. 7; fully complementary to ARK-2)

Mutant nucleic acid sequences:

ARK-2T-1: 5'CCC TCT CGG GG TATT GGG TCT GAC GAC3' (Seq. I.D. No. 15) (Lanes 4 & 9 ("$M_1^{10}$") in FIG. 7; contains a single base mismatch)

ARK-2T-2:

5'CCC TCT CGG GG TAAT GGG TCT GAC GAC3' (Seq. I.D. No. 16) (Lane 5 ("$M_2^{10}$") in FIG. 7; contains a double base mismatch)

ARK-2T-3:

5'CCC TCT CGG GG TAAA GGG TCT GAC GAC3' (Seq. I.D. No. 17) (Lane 6 ("$M_3^{10}$") in FIG. 7; contains a triple base mismatch)

ARK-2T-0:

5'CCC TCT CGG GGT GGG TCT GAC GAC3' (Seq. I.D. No. 18) (Lanes 7 & 10, [Δ]$^{10}$, in FIG. 7; contains a triple base deletion)

Figure 7:
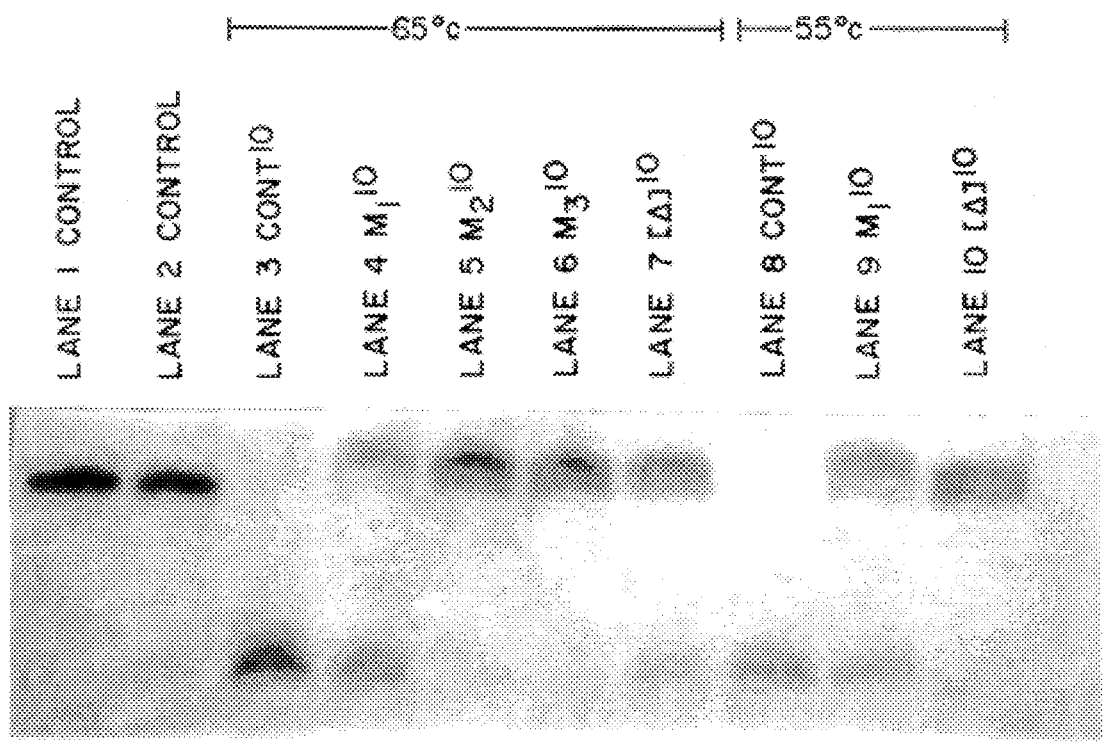
FIG. 7 depicts an autoradiogram of the results of an experiment using the method of the present invention to detect 1, 2, and 3-base mismatches and a 3-base deletion. Lane 1, control (nucleic acid probe only); Lane 2, control (nucleic acid probe and RNase H); Lane 3 and 8, "cont$^{10}$" contains a selected nucleic acid molecule that is fully complementary to the desired sequence in the nucleic acid probe; Lanes 4 and 9, "$M_1^{10}$" contains a selected nucleic acid molecule that has a 1-base mismatch; Lane 5, "$M_2^{10}$" contains a selected nucleic acid molecule that has a 2-base mismatch; Lane 6, "$M_3^{10}$" contains a selected nucleic acid molecule that has a 3-base mismatch; Lane 7 and 10, $[\Delta]^{10}$ contains a selected nucleic acid molecule that has a 3-base deletion. The reactions run in Lanes 3–7 were performed at 65° C.; the reactions run in Lanes 8–10 were performed at 55° C.

These nucleic acid molecules were used to produce the autoradiograph depicted in FIG. 7. Two controls were also used: Lane 1 ("$C_1$"), contained probe only, and Lane 2 ("$C_2$") contained probe plus RNase H (1 μl of a ⅒ dilution of a 1.67 μg/μl prep).

The reaction cocktail consisted of:

10 μls $^{32}$P-γ-ATP labeled ARK-2 probe

10 μls bovine serum albumin (BSA) at 10 mg/ml

10 μls 10× RNase-H buffer (0.5M Tris-HCl/100 mM MgCl$_2$)

50 μls dH$_2$O

This reaction mixture provided sufficient material for 8×10 μl reactions. All reactions contained a total of 10 pmoles of the appropriate selected nucleic acid molecule (present in 1 μl). The reaction cocktail was mixed with the control or selected nucleic acid molecule, and the resulting mixtures were incubated at 65° C. or 55° C. for 30 minutes. 10 μls of formamide loading dye (95% formamide; 0.1% bromophenol blue; 0.1% xylene cyanol) were then added to each reaction mixture, and the reactions were heated at 90° C. for 10 minutes. The reactions were then subjected to polyacrylamide (20% acrylamide/7M Urea) gel electrophoresis for 3 to 4 hours at 500 V.

EXAMPLE 6

THE EFFECT OF VARYING THE PROPORTION OF DESIRED NUCLEIC ACID SEQUENCE IN A SAMPLE

Figure 8:
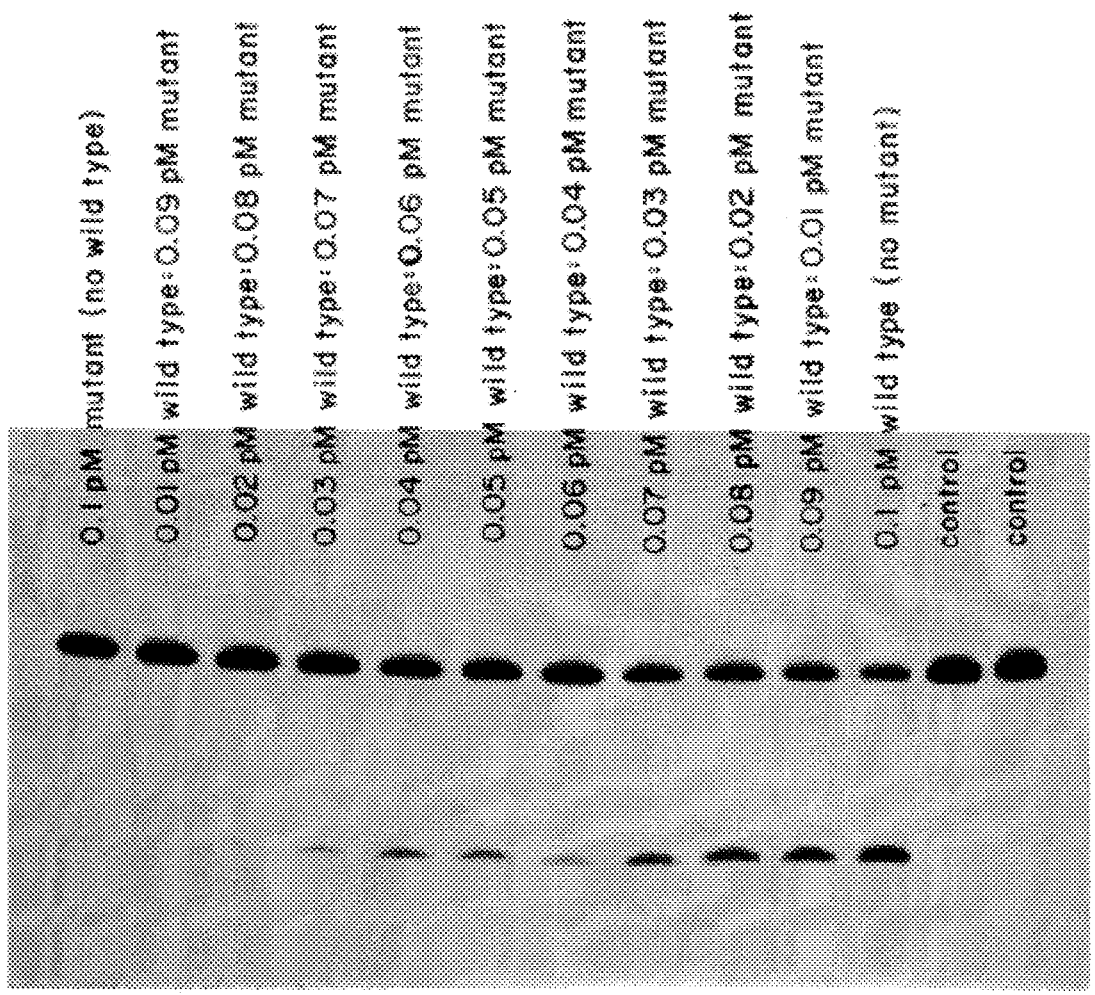
FIG. 8 depicts an autoradiogram of a quantitative study using the method of the present invention wherein different ratios of wild type ARK-2T to mutant ARK-2T-1. ARK-2T, which is identified as "CONT$^{10}$" in FIG. 7, represents a non-mutant selected nucleic acid molecule that is fully complementary to a desired sequence in a nucleic acid probe. ARK-2T-1, which is identified as "$M_1^{10}$" in FIG. 7, represents a mutant selected nucleic acid molecule having a 1-base mismatch. The probe was ARK-2, which is complementary to ARK-2T. The ratio of mutant:nonmutant in the reaction mixture ranged from 0.1 pM mutant (no wild type) to 0.1 pM wild type (no mutant), as follows. Lane 1: 0.1 pM mutant (no wild type). Lane 2: 0.01 pM wild type:0.09 pM mutant. Lane 3: 0.02 pM wild type:0.08 pM mutant. Lane 4: 0.03 pM wild type:0.07 pM mutant. Lane 5: 0.04 pM wild type:0.06 pM mutant. Lane 6: 0.05 pM wild type:0.05 pM mutant. Lane 7: 0.06 pM wild type:0.04 pM mutant. Lane 8: 0.07 pM wild type:0.03 pM mutant. Lane 9: 0.08 pM wild type:0.02 pM mutant. Lane 10: 0.09 pM wild type:0.01 pM mutant. Lane 11: 0.1 pM wild type (no mutant). Lanes 12 & 13: controls. The experimental conditions for FIG. 8 are the same as for FIG. 7, except that the reaction cocktail also included 10 µl of 18% of polyethylene glycol 8000 (PEG). The cycling reaction was carried out at 65° C.

FIG. 8 depicts an autoradiogram of a quantitative study of the present invention as applied to different proportions of desired nucleic acid sequence ($M_1^{10}$ in FIG. 7) in a sample. The proportion was varied relative to the concentration of a second nucleic acid sequence, ARK-2T (wild type) which varied from ARK-2T-1 (mutant) by a single base substitution. The proportions varied by 10% increments from 0.1 pmol wild type (ARK-2T) with no mutant to 0.1 pmol mutant (ARK-2T-1) with no wild type. Ten pmoles of the chimeric probe (ARK-2) was used to screen the reaction mixture. The results are depicted in FIG. 8. Experimental conditions were the same as described in Example 5 with the following exceptions: the reaction cocktail also included 10 μl of 18% polyethylene glycol 8000 (PEG) and the cycling reaction was carried out at 65° C.

Figure 9:
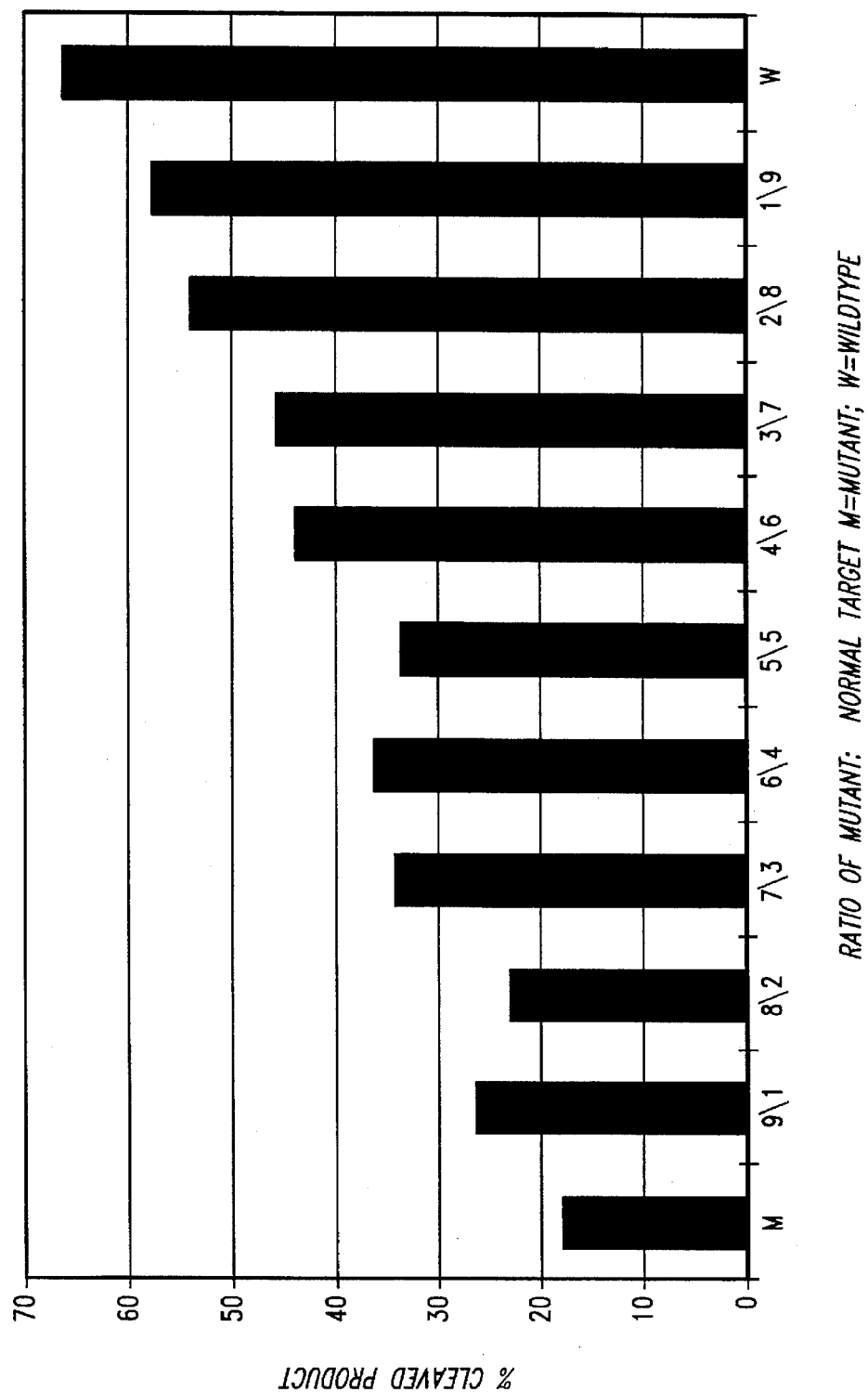
FIG. 9 depicts a histogram indicating the percentage of labeled probe in the autoradiogram of FIG. 8 that was cleaved.

FIG. 9 depicts a histogram indicating the relative quantity of the cleaved labeled probe in the autoradiogram of FIG. 8, using digitized data from a PhosphorImager (Molecular Dynamics) analyzed on an EXCEL PROGRAM, wherein the vertical axis indicates the percentage of the probe that was cleaved, and the horizontal axis indicates the ratio of mutant to wild type target in the reaction mixture. The results show that there is a definite increase in the amount of detectable cleaved probe fragments relative to an increased proportion of wild type to mutant target. Therefore, the results demonstrate that the present methods differentiate between a homozygous mutant, a heterozygote and a homozygous wild type.

EXAMPLE 7

DETECTION OF CYSTIC FIBROSIS INDUCING GENE MUTATION

The present invention can also be used to detect a mutation(s) in the transmembrane conductance regulator gene, which mutation tends to induce cystic fibrosis. Thus, the following nucleic acid probes are produced according to the methods set forth above:

Nucleic acid probes:

A455EN target (26-mer): 5'-CAA TAA GCA ACc gac CAC AAC CCC AG-3' (Seq. I.D. No. 19)

501–510N target (26-mer): 5'-AAA CAC CAA AGA tga tAT TTT CTT TGG-3' (Seq. I.D. No. 20)

In order to test the effectiveness of these nucleic acid probes, the following selected nucleic acid sequences are produced, to represent both nonmutant and mutant transmembrane conductance regulator genes.

Selected nucleic acid molecules (note, "N" indicates wild-type sequence):

A455E.N: 5'-CTG GGG TTG TGG TCG GTT GCT TAT TGT CTG CA-3' (Seq. I.D. No. 21)

A455E.M: 5'-CTG GGG TTG TGG TAG GTT GCT TAT TGT CTG CA-3' (Seq. I.D. No. 22)

501–510N: 5'-CAA AGA AAA TAT CAT CTT TGG TGT TTT CCT GCA-3' (Seq. I.D. No. 23)

Selected nucleic acid molecules having a three base pair deletion relative to native 501–510N target:

DI507.M: 5'-CAA AGA AAA TAT CTT TGG TGT TTT CCT GCA-3' (Seq. I.D. No. 24)

DI508.M: 5'-CAA AGA AAA TAT CAT TGG TGT TTT CCT GCA-3' (Seq. I.D. No. 25)

The reaction conditions are as set forth above. Detection of fragmented (cleaved) nucleic acid probe indicates the presence of a native or wild type gene. The amount of cleaved probe can be quantitated as set forth above to indicate whether the native gene, if present, is homozygous or heterozygous.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of determining whether a selected nucleic acid molecule contains a difference from a desired sequence comprising:

(a) incubating said selected nucleic acid molecule with a nucleic acid probe containing a scissile linkage, said nucleic acid probe being complementary at said scissile linkage to said desired sequence and the length of said scissile linkage determined by said difference, under conditions suitable for specific hybridization of said selected nucleic acid molecule with said nucleic acid probe to produce a hybrid;

(b) contacting said hybrid with an excising agent capable of cleaving said nucleic acid probe at said scissile linkage when said nucleic acid probe is specifically hybridized at said scissile linkage to said selected nucleic acid molecule, wherein upon cleavage of said nucleic acid probe at said scissile linkage one or more fragments of said nucleic acid probe adjacent to said scissile linkage are released from said hybrid; and (c) detecting and quantifying the rate of generation of said released fragments of said nucleic acid probe, and therefrom determining whether said selected nucleic acid molecule differs from said desired sequence.

2. A method according to claim 1 wherein said scissile linkage comprises RNA and said excising agent comprises RNase H.

3. A method according to claim 1 wherein said scissile linkage comprises DNA and the fragments of said nucleic acid probe adjacent to said scissile linkage comprise one or more of (a) modified DNA that cannot be effectively excised by said excising agent and (b) RNA.

4. A method according to claim 1 wherein said selected nucleic acid molecule is obtained from a diploid or polyploid organism.

5. A method according to claim 1 wherein said selected nucleic acid molecule is obtained from a haploid cell.

6. A method according to claim 1 wherein steps (a) through (c) are repeated utilizing a single selected nucleic acid molecule and multiple copies of said nucleic acid probe.

7. A method according to claim 1 wherein the length of said scissile linkage is from 0, 1 or 2 nucleotides longer on each side than said difference.

8. A method of determining whether a selected nucleic acid molecule contains a difference from a native nucleotide sequence, comprising:

(a) incubating said selected nucleic acid molecule with a nucleic acid probe containing a scissile linkage, said nucleic acid probe being complementary at said scissile linkage to said native nucleotide sequence and the length of said scissile linkage determined by said difference, under conditions suitable for specific hybridization of said selected nucleic acid molecule with said nucleic acid probe to produce a hybrid;

(b) contacting said hybrid with an excising agent capable of cleaving said nucleic acid probe at said scissile linkage when said nucleic acid probe is specifically hybridized at said scissile linkage to said selected nucleic acid molecule, wherein upon cleavage of said nucleic acid probe at said scissile linkage one or more fragments of said nucleic acid probe are released from said hybrid; and (c) detecting and quantifying the rate of generation of said released fragments of said nucleic acid probe, and therefrom determining whether said selected nucleic acid molecule differs from said native nucleotide sequence.

9. A method according to claim 8 wherein said selected nucleic acid molecule includes a somatic mutation at a site where said scissile linkage of said nucleic acid probe hybridizes.

10. A method according to claim 8 wherein said selected nucleic acid molecule is obtained from an oncogene.

11. A method according to claim 8 wherein said selected nucleic acid molecule includes a germ line mutation at a site where said scissile linkage of said nucleic acid probe hybridizes.

12. A method according to claim 8 wherein said selected nucleic acid molecule comprises at least a portion of the transmembrane conductance regulator gene.

13. A method according to claim 8 wherein the length of said scissile linkage is from 0, 1 or 2 nucleotides longer on each side than said difference.

14. A method of determining whether a selected nucleic acid molecule contains a suspected difference from a desired sequence comprising:

in a first reaction vessel:

(a) incubating said selected nucleic acid molecule with a first nucleic acid probe containing a scissile linkage, said first nucleic acid probe being complementary at said scissile linkage to said desired sequence and the length of said scissile linkage determined by said suspected difference, under conditions suitable for specific hybridization of said selected nucleic acid molecule with said first nucleic acid probe to produce a hybrid;

(b) contacting said hybrid with an excising agent capable of cleaving said first nucleic acid probe at said scissile linkage when said first nucleic acid probe is specifically hybridized at said scissile linkage to said selected nucleic acid molecule, wherein upon cleavage of said first nucleic acid probe at said scissile linkage one or more fragments of said first nucleic acid probe are released from said hybrid; and in a second reaction vessel:

(c) incubating said selected nucleic acid molecule with a second nucleic acid probe containing a scissile linkage, said second nucleic acid probe being complementary at said scissile linkage to said suspected difference and the length of said scissile linkage determined by said suspected difference, under conditions suitable for specific hybridization of said selected nucleic acid molecule with said second nucleic acid probe to produce a hybrid;

(d) contacting said hybrid with an excising agent capable of cleaving said second nucleic acid probe at said scissile linkage when said second nucleic acid probe is specifically hybridized at said scissile linkage to said selected nucleic acid molecule, wherein upon cleavage of said second nucleic acid probe at said scissile linkage one or more fragments of said second nucleic acid probe are released from said hybrid; and then (e) detecting and quantifying the generation of said released fragments of said first nucleic acid probe and said second nucleic acid probe, comparing said detection and quantification, and therefrom determining whether said selected nucleic acid molecule differs from said desired sequence.

15. A method according to claim 14 wherein said desired sequence corresponds to a native sequence.

16. A method according to claim 14 wherein the length of said scissile linkage of each of said first nucleic acid probe and said second nucleic acid probe is from 0, 1 or 2 nucleotides longer on each side than said suspected difference.

17. A method of determining whether a product of a selected nucleic acid molecule tends to induce cystic fibrosis by determining whether the selected nucleic acid molecule has a difference from a native nucleotide sequence for the transmembrane conductance regulator gene, the method comprising:

(a) incubating said selected nucleic acid molecule with a nucleic acid probe containing a scissile linkage, the length of said scissile linkage determined by said suspected difference, and said nucleic acid probe complementary at said scissile linkage to said native nucleotide sequence for the transmembrane conductance regulator gene, under conditions suitable for hybridization of said selected nucleic acid molecule with said nucleic acid probe to produce a hybrid;

(b) contacting said hybrid under said conditions with an excising agent capable of cleaving said nucleic acid probe at said scissile linkage when said nucleic acid probe is specifically hybridized at said scissile linkage to said selected nucleic acid molecule, wherein upon cleavage of said nucleic acid probe at said scissile linkage one or more fragments of said nucleic acid probe are released from said hybrid; and (c) detecting and quantifying the rate of generation of said released fragments of said nucleic acid probe, and therefrom determining whether said selected nucleic acid molecule differs from said native nucleotide sequence, thereby indicating that said selected nucleic acid molecule tends to induce cystic fibrosis.

18. A method according to claim 17 wherein said selected nucleic acid molecule is obtained from a diploid animal and wherein said determining step further comprises determining whether said organism is (a) homozygous in both alleles for a mutation in the transmembrane conductance regulator gene, (b) heterozygous with one allele having a mutation in the transmembrane conductance regulator, and the other allele containing the native nucleotide sequence transmembrane conductance regulator gene, or (c) homozygous in both alleles for the native nucleotide sequence transmembrane conductance regulator gene.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_RNA
        ( B ) LOCATION: 8..11

( x i ) SEQUENCE DESCRIPTION: SEQ ID NO:1:

CATCACCGGA ATTGAAGCC            19

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGCTTCAATT CCGGTGATG            19

( 2 ) INFORMATION FOR SEQ ID NO:3:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:3:

TTGCTCGGTG ATGCCCAGCG CCGAATTC                28

( 2 ) INFORMATION FOR SEQ ID NO:4:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

GAATTCGGCG CTGGGCATCA CCGAGCAA                28

( 2 ) INFORMATION FOR SEQ ID NO:5:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

CGTCGGGCGC AGCCCACGGG ACGCGGCAGG              30

( 2 ) INFORMATION FOR SEQ ID NO:6:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

CCTGCCGCGT CCCGTGGGCT GCGCCCGACG              30

( 2 ) INFORMATION FOR SEQ ID NO:7:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

CCGAATTCTT ATGCCTCTTC GTGA                    24

( 2 ) INFORMATION FOR SEQ ID NO:8:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

CCGAATTCAA CCCCTCCCCC AGGA                    24

( 2 ) INFORMATION FOR SEQ ID NO:9:

( i ) SEQUENCE CHARACTERISTICS:

(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:9:

CCGAATTCCC TCCCCCAGGA AAC 23

(2) INFORMATION FOR SEQ ID NO:10:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:10:

CCGCATATGA ACCCCTCCCC CAGG 24

(2) INFORMATION FOR SEQ ID NO:11:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:11:

AAGGTGAATT CAATGAACCC CTCCCCCAGG 30

(2) INFORMATION FOR SEQ ID NO:12:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:12:

ACCAAGCTTC TTATGCCTCT TCGTGAA 27

(2) INFORMATION FOR SEQ ID NO:13:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(A) NAME/KEY: misc_RNA
(B) LOCATION: 13..16

(xi) SEQUENCE DESCRIPTION: SEQ ID NO:13:

GTCGTCAGAC CCAAAACCCC GAGAGGG 27

(2) INFORMATION FOR SEQ ID NO:14:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:14:

CCCTCTCGGG GTTTTGGGTC TGACGAC 27

(2) INFORMATION FOR SEQ ID NO:15:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (xi) SEQUENCE DESCRIPTION: SEQ ID NO:15:

CCCTCTCGGG GTATTGGGTC TGACGAC      27

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:16:

CCCTCTCGGG GTAATGGGTC TGACGAC      27

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:17:

CCCTCTCGGG GTAAAGGGTC TGACGAC      27

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:18:

CCCTCTCGGG GTGGGTCTGA CGAC      24

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: misc_RNA
        (B) LOCATION: 12..15

(xi) SEQUENCE DESCRIPTION: SEQ ID NO:19:

CAATAAGCAA CCGACCACAA CCCCAG      26

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (A) NAME/KEY: misc_RNA
        (B) LOCATION: 13..16

(x i) SEQUENCE DESCRIPTION: SEQ ID NO:20:

AAACACCAAA GATGATATTT TCTTTGG 27

(2) INFORMATION FOR SEQ ID NO:21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (x i) SEQUENCE DESCRIPTION: SEQ ID NO:21:

CTGGGGTTGT GGTCGGTTGC TTATTGTCTG CA 32

(2) INFORMATION FOR SEQ ID NO:22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (x i) SEQUENCE DESCRIPTION: SEQ ID NO:22:

CTGGGGTTGT GGTAGGTTGC TTATTGTCTG CA 32

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (x i) SEQUENCE DESCRIPTION: SEQ ID NO:23:

CAAAGAAAAT ATCATCTTTG GTGTTTTCCT GCA 33

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:24:

CAAAGAAAAT ATCTTTGGTG TTTTCCTGCA 30

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:25:

CAAAGAAAAT ATCATTGGTG TTTTCCTGCA 30